(12) United States Patent
He et al.

(10) Patent No.: US 8,969,513 B2
(45) Date of Patent: Mar. 3, 2015

(54) CASPOFUNGIN ANALOG AND APPLICATIONS THEREOF

(75) Inventors: Bingming He, Shanghai (CN); Ming Li, Shanghai (CN); Zhijun Tang, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/884,750

(22) PCT Filed: Nov. 10, 2011

(86) PCT No.: PCT/CN2011/082022
§ 371 (c)(1),
(2), (4) Date: May 10, 2013

(87) PCT Pub. No.: WO2012/062213
PCT Pub. Date: May 18, 2012

(65) Prior Publication Data
US 2013/0296229 A1    Nov. 7, 2013

(30) Foreign Application Priority Data

Nov. 10, 2010   (CN) .......................... 2010 1 0538954

(51) Int. Cl.
C07K 7/56 (2006.01)
A61K 38/12 (2006.01)
A61K 38/00 (2006.01)

(52) U.S. Cl.
CPC . *C07K 7/56* (2013.01); *A61K 38/12* (2013.01); *A61K 38/00* (2013.01)
USPC ............. 530/317; 514/2.9; 514/3.6; 514/21.1

(58) Field of Classification Search
None
See application file for complete search history.

(56) References Cited

U.S. PATENT DOCUMENTS

2010/0168415 A1 *   7/2010   Lee et al. ...................... 540/460

FOREIGN PATENT DOCUMENTS

| WO | WO 9624613 A1 * | 8/1996 |
| WO | WO 02083713 A2 * | 10/2002 |
| WO | 2009142761 A1 | 11/2009 |

OTHER PUBLICATIONS

International Search Report from Application PCT/CN2011/082022, dated Feb. 16, 2012, 3 pages.

* cited by examiner

*Primary Examiner* — Jeffrey E Russel
(74) *Attorney, Agent, or Firm* — Hamre, Schumann, Mueller & Larson, P.C.

(57) ABSTRACT

Disclosed are a caspofungin analog and applications thereof. The caspofungin analog is a compound having a structure as indicated in Formula (4), or pharmaceutically acceptable salts thereof. $R_1$ can be chosen from hydroxyl, benzyloxy, phenoxy, substituted phenoxy, or substituted benzyloxy. $R_2$, $R_3$, $R_4$, $R_5$ can be chosen from hydrogen, C1-C6 alkyl, C1-C6 alkoxy, hydroxyl, benzyloxyphenyl, substituted benzyloxyphenyl, nitro, fluorine, chlorine, bromine, or iodine. Also disclosed are a preparation method for and applications of the compound.

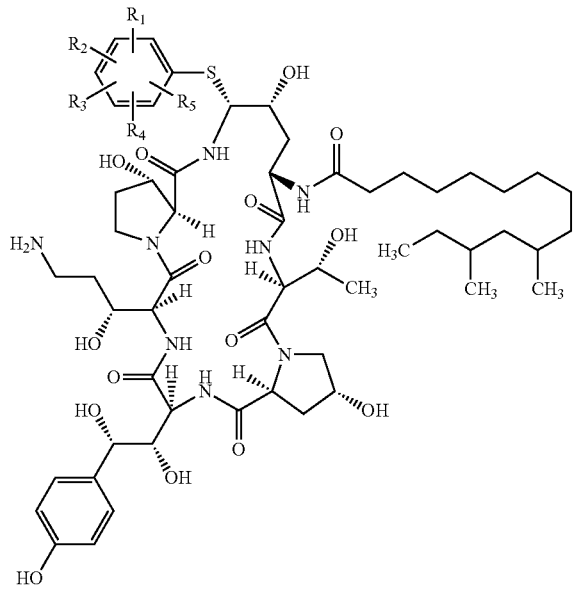

22 Claims, No Drawings

CASPOFUNGIN ANALOG AND APPLICATIONS THEREOF

TECHNICAL FIELD

The present invention relates to the field of organic chemistry, particularly to a Caspofungin analog, or the pharmaceutically acceptable salts thereof as well as the preparation method thereof.

BACKGROUND

In 1974, it was discovered that echinocandin compounds possess excellent antibacterial activity. And then, many semi-synthetic echinocandin compounds have been studied for their pharmacologic activities. In 2001, caspofungin was approved by FDA of the United States, which represents the landmark for the research of antifungal medicaments. Caspofungin, the chemical structure of which is shown by Formula 1, represents a broad-spectrum and low-toxic medicament with unique action site:

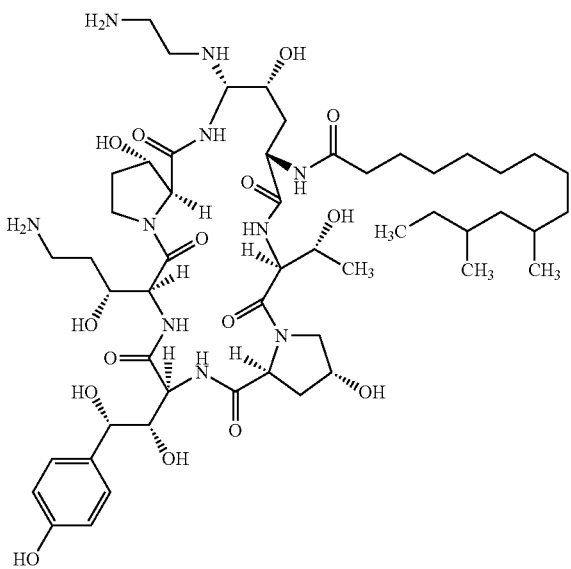

1

Caspofungin analogs and the preparation of Caspofungin have been described in WO94/21677, EP620232, WO96/24613, U.S. Pat. No. 5,552,521, WO97/47645, U.S. Pat. No. 5,936,062, WO02/083713, J. Org. Chem., 2007, 72, 2335-2343, CN101792486A, CN 101648994A, WO2010008493A2, US2010168415A1, EP1785432, and WO2010064219A1.

In WO94/21677 and EP 620232, the method for synthesizing and purifying caspofungin has been disclosed, comprising the following steps: Pneumocandin $B_0$ as the starting material reacts with alkyl thiol or aryl thiol, the resulting product is oxidized to obtain the sulfone intermediate, and then the sulfone intermediate reacts with amines in anhydrous non-protonic solvent to obtain caspofungin, which was purified by chromatography.

According to WO96/24613 and US5552521, the primary amide group in Pneumocandin $B_0$ is reduced to amine group (47% of yield), and then the resulting product reacts with thiophenol and ethylenediamine in turn to obtain caspofungin.

In WO97/47645, U.S. Pat. No. 5,936,062 and J. Org. Chem., 2007, 72, 2335-2343, two stereoselective methods for preparing caspofungin from Pneumocandin $B_0$ have been reported. In the first method, phenyl borate is used as protective group, the amide group in Pneumocandin $B_0$ is reduced to amine group, and then the resulting product reacts with thiophenol and ethylenediamine in turn to obtain the caspofungin; in the second method, Pneumocandin $B_0$ as the starting material reacts with thiophenol, the resulting product is protected by phenyl borate, the amide group in Pneumocandin $B_0$ is reduced to amine group, and then the resulting product reacts with ethylenediamine to obtain caspofungin.

In CN101792486A and CN 101648994A, a method has been disclosed, comprising the following steps: Pneumocandin $B_0$ as the starting material reacts with ethylenediamine under the protection of phenyl borate, and then the amide group in the resulting intermediate is reduced to amine group to obtain caspofungin.

In WO02/083713, US2010168415A1, EP1785432, WO2010064219A1, WO2010061219A1, a method has been disclosed, comprising the following steps: the intermediate of Pneumocandin $B_0$ containing cyano is prepared, and then the intermediate is reduced by using hydrogen to obtain caspofungin.

According to WO2010008493A2, Pneumocandin $B_0$ as the starting material reacts with 4-methoxy thiophenol, the resulting product is protected by phenyl borate, the amide group in Pneumocandin $B_0$ is reduced to amine group under the condition of dehydration by 3 A molecular sieve, and then the resulting product reacts with ethylenediamine to obtain caspofungin.

However, for the yield, purity, stability and waste, none of the disclosed methods is the optimal method for industrialization. The cost for industrialization will be greatly increased due to the repeated use of chromatographic column for many times, thus resulting in great amount of waste. Some methods must be conducted under strict anhydrous conditions (such as, dehydration by 3 A molecular sieve). Most of the methods which use thiophenol with odor and high toxicity, are difficult to be operated, harmful to the operator and severely pollute the environment. Additionally, in some of the existing synthetic methods, isomers will be inevitably produced during the preparation of Pneumocandin $B_0$ containing cyano, the stereoselectivity and yield are not high, and expensive metals are used as catalysts, thereby resulting in high cost for industrialization. Therefore, it is urgent to develop a method for preparing caspofungin which is suitable for industrialization.

SUMMARY OF THE INVENTION

The subject of the present invention is to provide a caspofungin analog or the pharmaceutically acceptable salts thereof.

Another subject of the present invention is to provide a preparation method for the caspofungin analog.

Another subject of the present invention is to provide uses of the caspofungin analog.

In the first aspect of the invention, the compound of Formula 4 or the pharmaceutically acceptable salts thereof is provided,

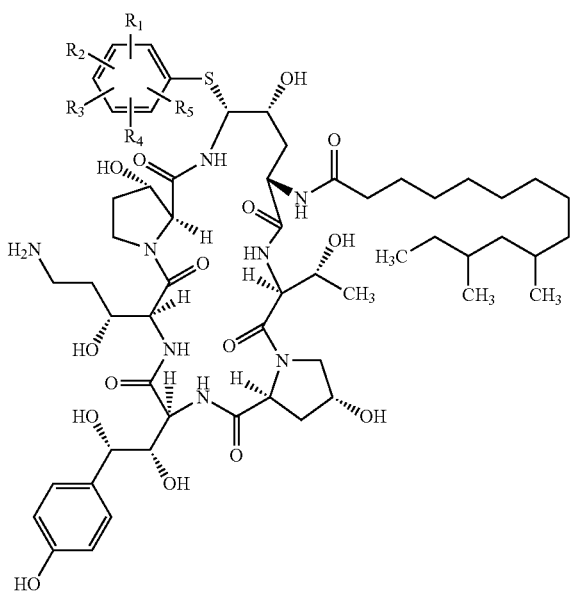

4

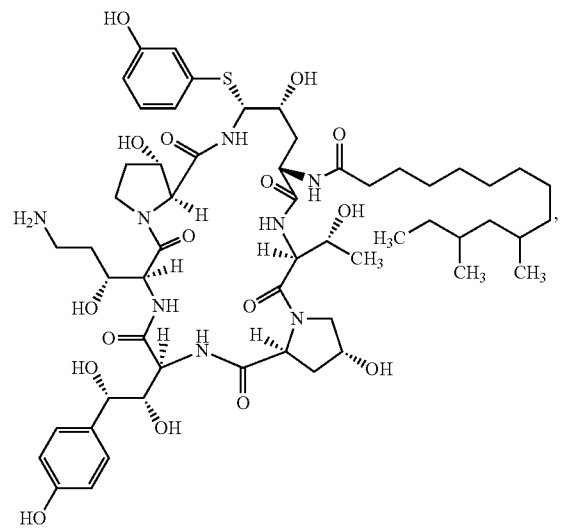

4b wherein $R_1$ is selected from hydroxy, benzyloxy, phenoxy, or substituted phenoxy, or substituted benzyloxy; $R_2$, $R_3$, $R_4$, $R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively.

Preferably, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro.

More preferably, $R_1$ is selected from hydroxy; $R_2$, $R_3$, $R_4$, $R_5$ is selected from hydrogen, methyl, or hydroxyl.

In another preferred example, the compound is the compound of Formula 4a, 4b, 4c, 4d, or 4e:

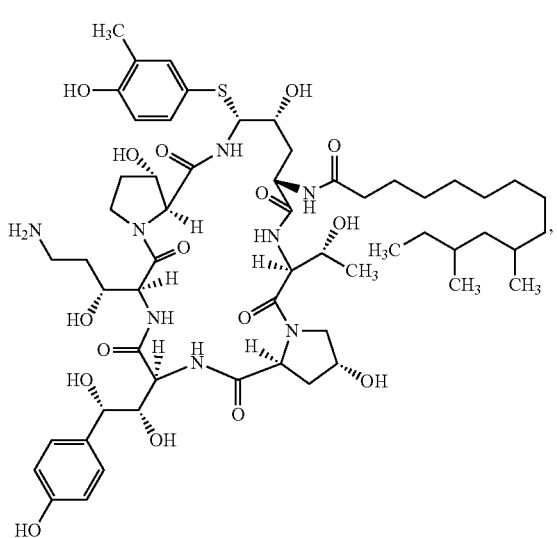

4c

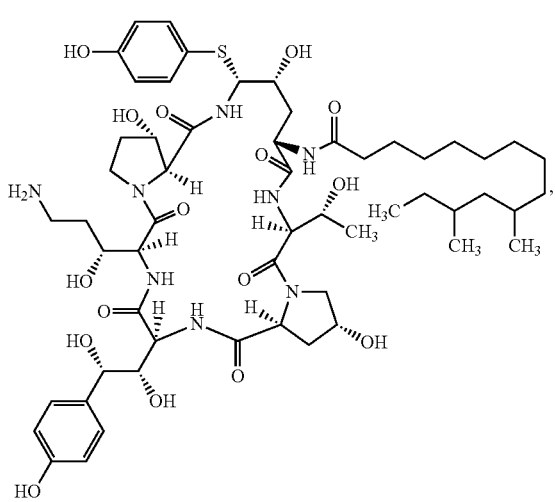

4a

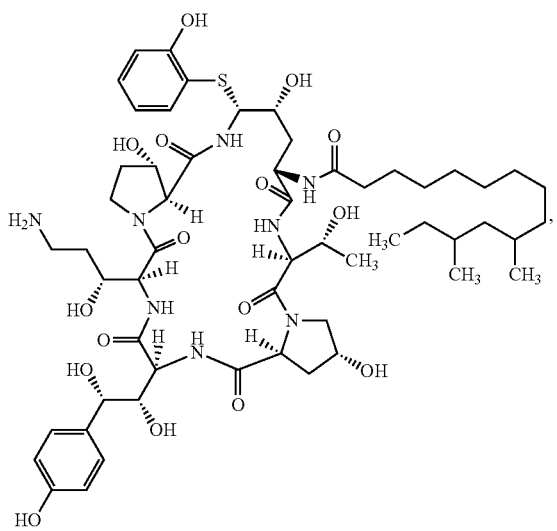

4d

-continued

4e

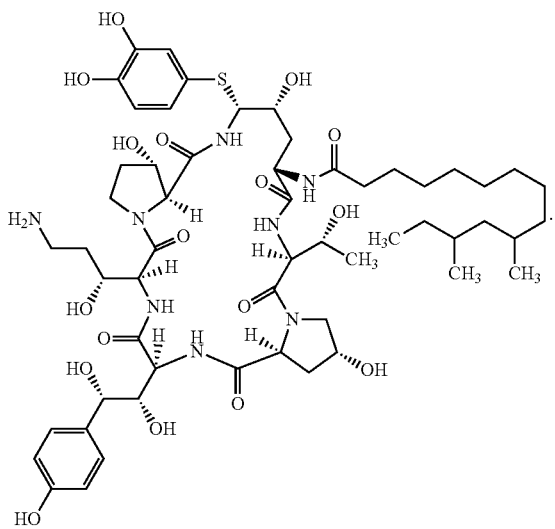

In another preferred example, the compound is the compound of Formula 4a.

In the second aspect of the invention, a preparation method for the compound of Formula 4 or the pharmaceutically acceptable salts thereof is provided, said method comprising the following steps:

(a) mixing the compound of Formula 2 with strong leaving-group compound 5, thereby obtaining the compound of Formula 3; and (b) mixing the compound of Formula 3 with a hydroxyl protectant, and then with a borane complex to obtain the compound of Formula 4;

2

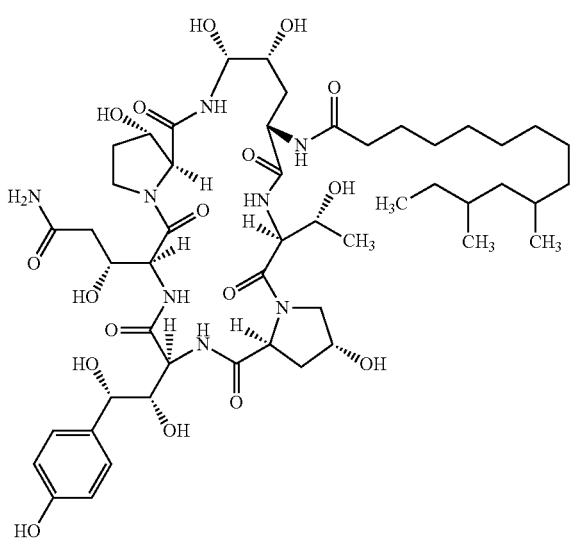

-continued

3

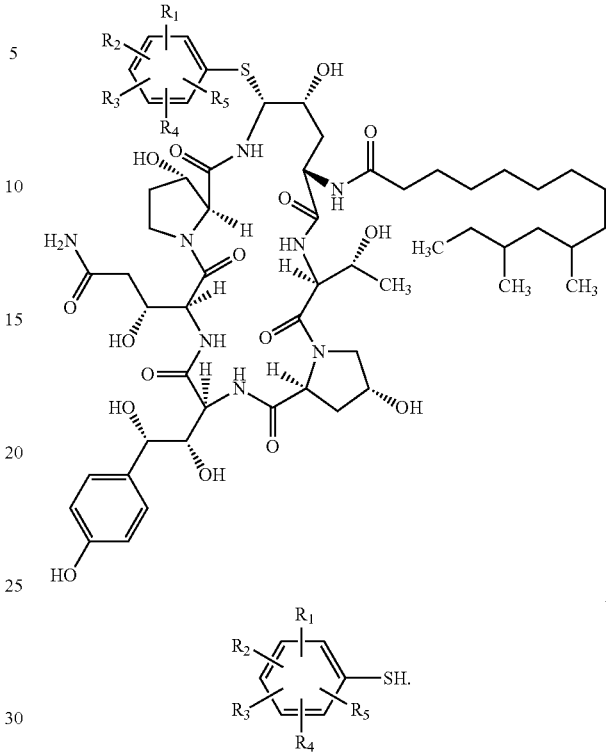

5

In step (a) of the above method, in the strong leaving-group compound 5, $R_1$ is selected from hydroxy, benzyloxy, phenoxy, or substituted phenoxy, or substituted benzyloxy; $R_2$, $R_3$, $R_4$, $R_5$ is selected from hydrogen, C1-C6 alkyl, C1-C6 alkoxy, hydroxy, benzyloxyphenyl, substituted benzyloxyphenyl, nitro, fluorine, chlorine, bromine, or iodine, respectively. Preferably, in the sulphydryl-substituted aromatic ring compound 5, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro. More preferably, in the sulphydryl-substituted aromatic ring compound 5, $R_1$ is selected from hydroxy; $R_2$, $R_3$, $R_4$, $R_5$ is selected from hydrogen, methyl, or hydroxyl. Most preferably, the sulphydryl-substituted aromatic ring compound 5 is selected from 4-hydroxy thiophenol.

In the above method, the strong leaving-group compound 5 is mixed with an acid, wherein said acid is selected from trifluoroacetic acid, triflic acid, camphor sulfonic acid, methanesulfonic acid or p-toluene sulphonic acid.

In step (a) of the above method, the temperature for mixing is −50° C. to 40° C.; preferably, −20° C. to −15° C.

In step (b) of the above method, the hydroxyl protectant is selected from boric acid protectants or silicane agents.

In step (b) of the above method, the borane complex is selected from: the complex of borane and tetrahydrofuran, borane and dimethyl sulfide, borane and diphenyl sulfide, borane and dibenzyl sulfide, borane and dioxane, borane and 1,4-oxathiane, or the complex of $BH_2Cl$ and dimethyl sulfide; preferably, the complex of borane and tetrahydrofuran, or borane and dimethyl sulfide.

In the third aspect of the invention, the use of the compound of the present invention or the pharmaceutically acceptable salts thereof for preparing the compound of Formula 1 is provided,

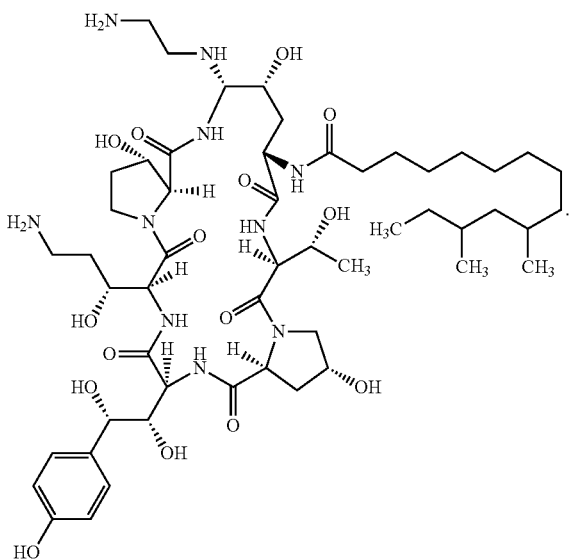

In the fourth aspect of the invention, the preparation method for the compound of Formula 1 is provided, said method comprising the following steps: mixing the compound of Formula 4 with ethylenediamine to obtain the compound of Formula 1.

In another preferred example, the compound of Formula 4 is mixed with ethylenediamine dissolved in the solvent selected from the following group: methanol, ethanol, tetrahydrofuran, 2-methyl tetrahydrofuran, isopropanol, trifluoroethanol, acetonitrile or dichloromethane; and the temperature for mixing is 0° C. to 40° C.; preferably, 25° C. to 35° C.

In another preferred example, a preparation method for the compound of Formula 1 is provided, said method comprising the following steps:

(a) mixing the compound of Formula 2 with strong leaving-group compound 5, thereby obtaining the compound of Formula 3;

(b) mixing the compound of Formula 3 with a hydroxyl protectant, and then with a borane complex to obtain the compound of Formula 4; and (c) mixing the compound of Formula 4 with ethylenediamine to obtain the compound of Formula 1.

In the fifth aspect of the invention, the use of the compound of Formula 4 or the pharmaceutically acceptable salts thereof for preparing the medicaments for preventing or treating the diseases caused by fungi infection is provided.

In the sixth aspect of the invention, a pharmaceutical composition is provided, said composition comprising the compound of Formula 4 or the pharmaceutically acceptable salts thereof and pharmaceutically acceptable carriers.

Based on the above, a preparation method for caspofungin suitable for industrialization is provided.

DETAILED DESCRIPTION OF THE INVENTION

The inventors have discovered a simple method for preparing the compound of Formula 4. Through a great deal of experiments, the inventors have discovered that the compound of Formula 1, i.e., caspofungin, can be readily obtained from the compound of Formula 4 through aminolysis using ethylenediamine.

As used herein, chemical formulae or names should include all of the optical isomers and stereoisomers, as well as the mixture or racemic mixture comprising the isomers.

PREPARATION METHOD

In the present invention, a preparation method for the compound of formula 1 is provided, said method comprising the following steps:

in the first step, the compound of Formula 2 is mixed with the strong leaving-group compound 5 to obtain the compound of Formula 3;

afterwards, the compound of Formula 3 is mixed with a hydroxyl protectant, and then with a borane complex to obtain the compound of Formula 4, and the compound of Formula 4 is mixed with ethylenediamine to obtain the compound of Formula 1.

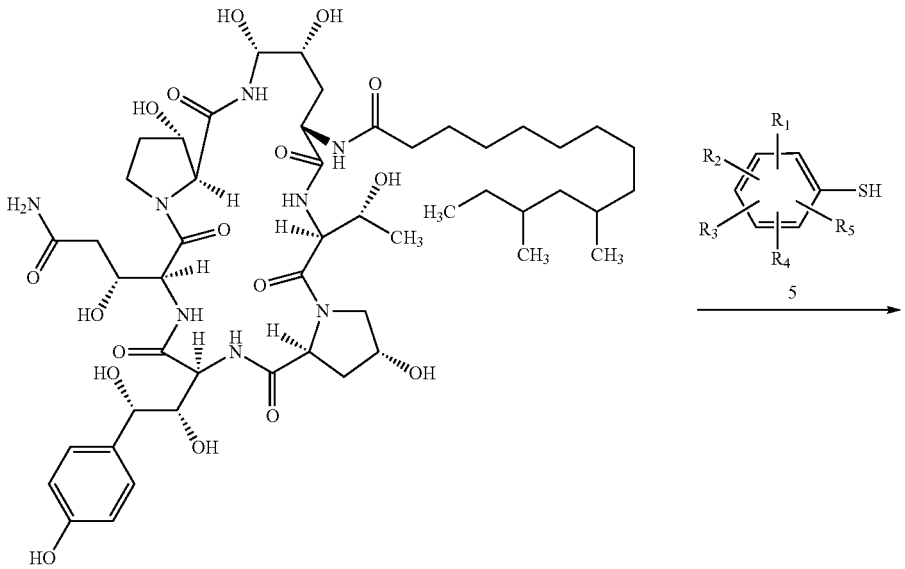

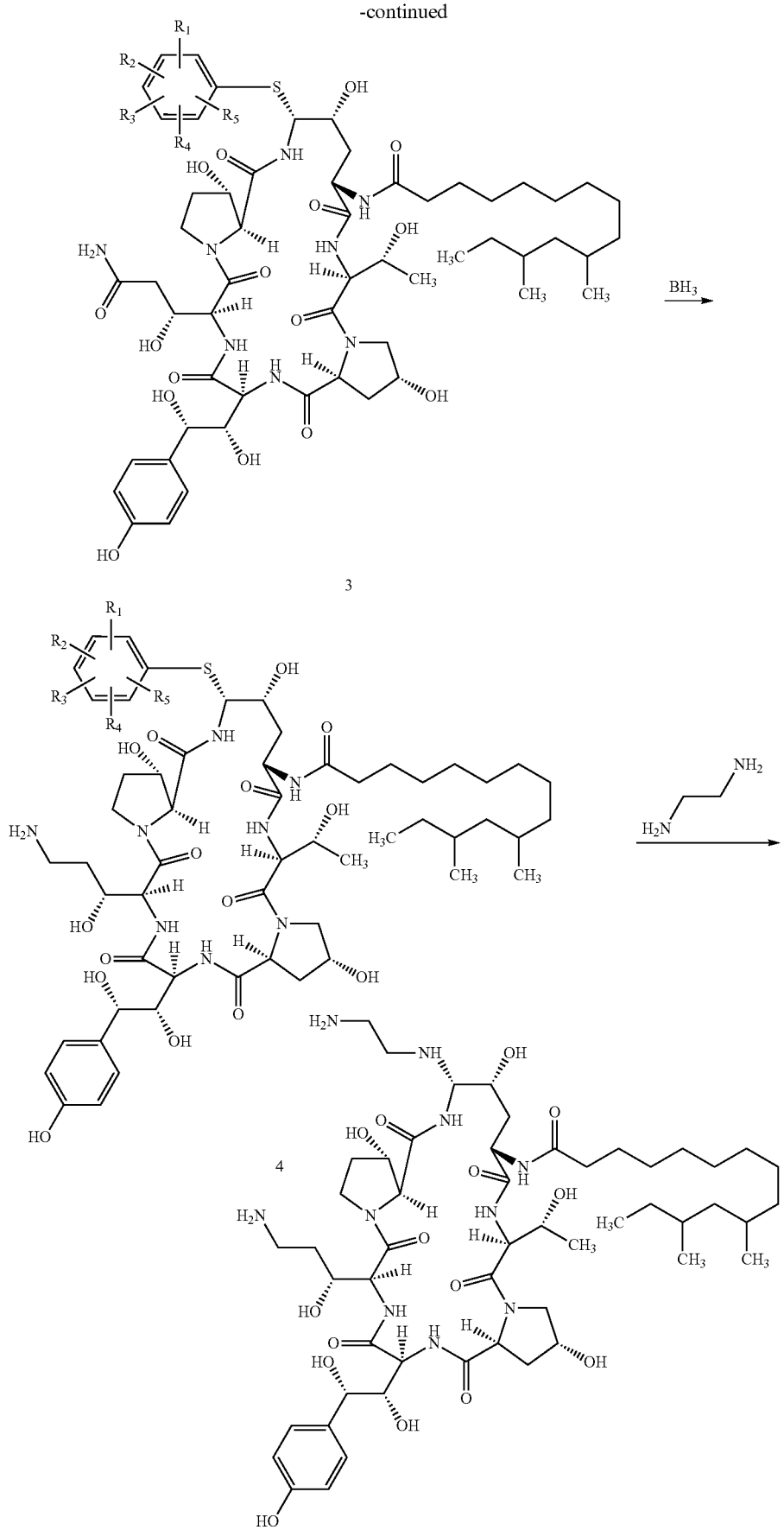

In the preparation method provided by the present invention, the starting material, i.e., the compound of Formula 2, can be obtained by the methods well-known in the art, for example (but not limited to), U.S. Pat. No. 5,021,341 (published on Jun. 4, 1991), culturing Zalerion arboricola ATCC 20868 in a medium rich in mannitol as the major carbon source.

In the present invention, the strong leaving-group compound is sulphydryl-substituted aromatic ring compound 5, wherein $R_1$ is selected from hydroxy, benzyloxy, phenoxy, substituted phenoxy, or substituted benzyloxy; $R_2$, $R_3$, $R_4$, $R_5$ is selected from hydrogen, C1-C6 alkyl, C1-C6 alkoxy, hydroxyl, benzyloxyphenyl, substituted benzyloxyphenyl, nitro, fluorine, chlorine, bromine, or iodine, respectively. Preferably, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro. More preferably, $R_1$ is selected from hydroxy; $R_2$, $R_3$, $R_4$, $R_5$ is selected from hydrogen, methyl, or hydroxyl. Most preferably, aromatic ring compound 5 is selected from 4-hydroxy thiophenol.

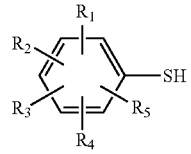

5

In the first step, the catalyst can be any acid with moderate intensity, for example (but not limited to) trifluoroacetic acid, triflic acid, camphor sulfonic acid, methanesulfonic acid or p-toluene sulphonic acid; preferably, triflic acid.

In one example of the present invention, the reaction of the first step can be conducted by reacting the compound of Formula 2 with 4-hydroxy thiophenol dissolved in acetonitrile and trifluoroacetic acid to produce the hydroxyl-substituted diphenyl sulfide intermediate, i.e., the compound of Formula 3. The reaction solution is neutralized by aqueous sodium acetate and then the stable intermediate in solid can be obtained.

According to one example of the present invention, in the reaction of the first step, phenyl boronic acid can be added to protect two adjacent hydroxyls in homotyrosine segment, thereby producing the phenyl borate intermediate 6, thereby significantly reducing the amount of the impurity, i.e., diphenyl sulfide compound 7. The temperature for reaction can also be reduced. Preferably, when phenyl boronic acid is used to protect the adjacent hydroxyls, a stronger acid, for example, triflic acid can be used as the catalyst.

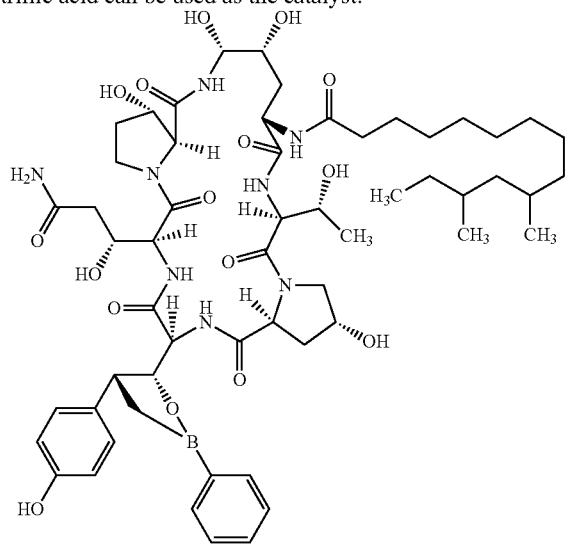

6

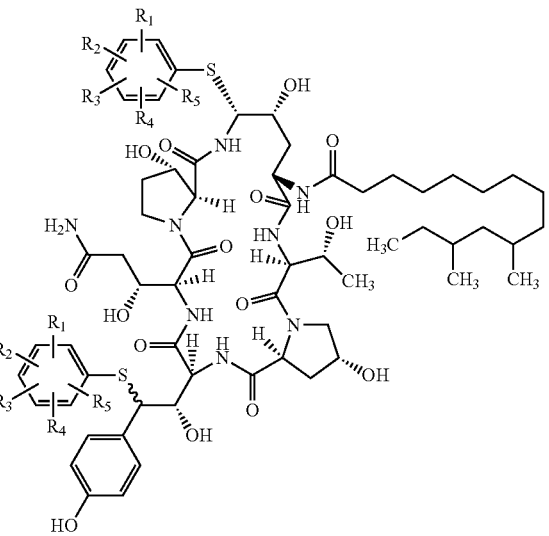

7

The amount of the final product depends on the amount of the compound 5 in this step. The highest production of the final product can be obtained at 3-5 equivalent.

In one preferred example of the present invention, 3-5 equivalent of 4-hydroxy thiophenol is used in the reaction of the first step. The preferable condition for forming sulfide is that 3 equivalent of 4-hydroxy thiophenol, 2 equivalent of phenyl boronic acid and 3 equivalent of triflic acid are dissolved in acetonitrile at −15° C., and the yield for the solid is 90-95%.

According to one example of the present invention, in the second step, the compound of Formula 3 is mixed with a hydroxyl protectant, and then with a borane complex in polar solvent to obtain the compound of Formula 4.

The reductant is selected from borane complex, or metal boride, titanium or zirconium boride dissolved in THF or other suitable solvents, or the complex of borane and ammonia, dimethylamine, pyridine or piperazine. The preferred reductant is borane complex, which can be selected from the complex of borane and tetrahydrofuran, dimethyl sulfide, diphenyl sulfide, dibenzyl sulfide, dioxane, or 1,4-oxathiane, or the complex of $BH_2Cl$ and dimethyl sulfide; preferably, the complex of borane and tetrahydrofuran, or borane and dimethyl sulfide. The metal boride dissolved in THF or other suitable solvents is selected from the complex of $ZrCh_4$/$NaBH_4$ or $TiCl_4$/$NaBH_4$. The raw material which is not reduced to amine by the reductant can be separated by reverse-phase chromatography.

In one preferred example of the present invention, the two adjacent hydroxyls in homotyrosine segment are protected in advance, N,O-bis(trimethylsilyl)trifluoroacetamide (BSTFA) is used to protect the remaining hydroxyls and amino to obtain the homogeneous reaction solution, thereby significantly increasing the yield for the reaction. The preferred conditions are listed as follows: at 10° C. to 68° C., the compound of Formula 4 reacts with 1.1-3.0 equiv of phenyl boric acid in tetrahydrofuran, and then 3-9 equiv of BSTFA is added at 0° C. to 68° C. to obtain the homogeneous reaction solution, borane is added at −30° C. to 30° C. to obtain the crude compound of formula 4, the reaction is quenched by hydrochloric acid, and then the purified compound of Formula 1 is obtained by column chromatography and crystallization.

According to one example of the present invention, in the third step, the compound of Formula 4 reacts with ethylenediamine in a polar solvent to obtain the compound of Formula 1.

Preferably, the reaction can be conducted at the temperature of 0° C. to 40° C. for 0.5-96 hours. More preferably, the reaction can be conducted at the room temperature for 24-72 hours.

Preferably, the polar solvent is selected from methanol, ethanol, tetrahydrofuran, 2-methyl tetrahydrofuran, isopropanol, trifluoroethanol, acetonitrile or dichloromethane with methanol and ethanol being preferred.

In the examples provided in the present invention, after the third step is completed, acetic acid is used for regulating pH to 4-6, the reaction solution is diluted by water, and the dry caspofungin in solid (i.e., the compound of Formula 1) is obtained by column chromatography, concentration or crystallization.

After the reaction is completed, acetic acid is used for regulating pH to 4-6, the reaction solution is diluted by water, and the dry intermediate in solid (i.e., the compound of Formula 1) is obtained by column chromatography, concentration or crystallization. In a preferred example of the present invention, the column chromatography is performed on reverse-phase column, and the aqueous organic solvent is used to elute the column. The organic solvent is selected from methanol, acetonitrile, ethanol, isopropanol and the like, with acetonitrile being preferred.

USE

An important use for the compound of Formula 4 provided in the present invention is that it can be used as the intermediate for obtaining caspofungin, i.e., the compound of Formula 1. That is, aminolysis is applied to the compound of Formula 4 using ethylenediamine to obtain caspofungin.

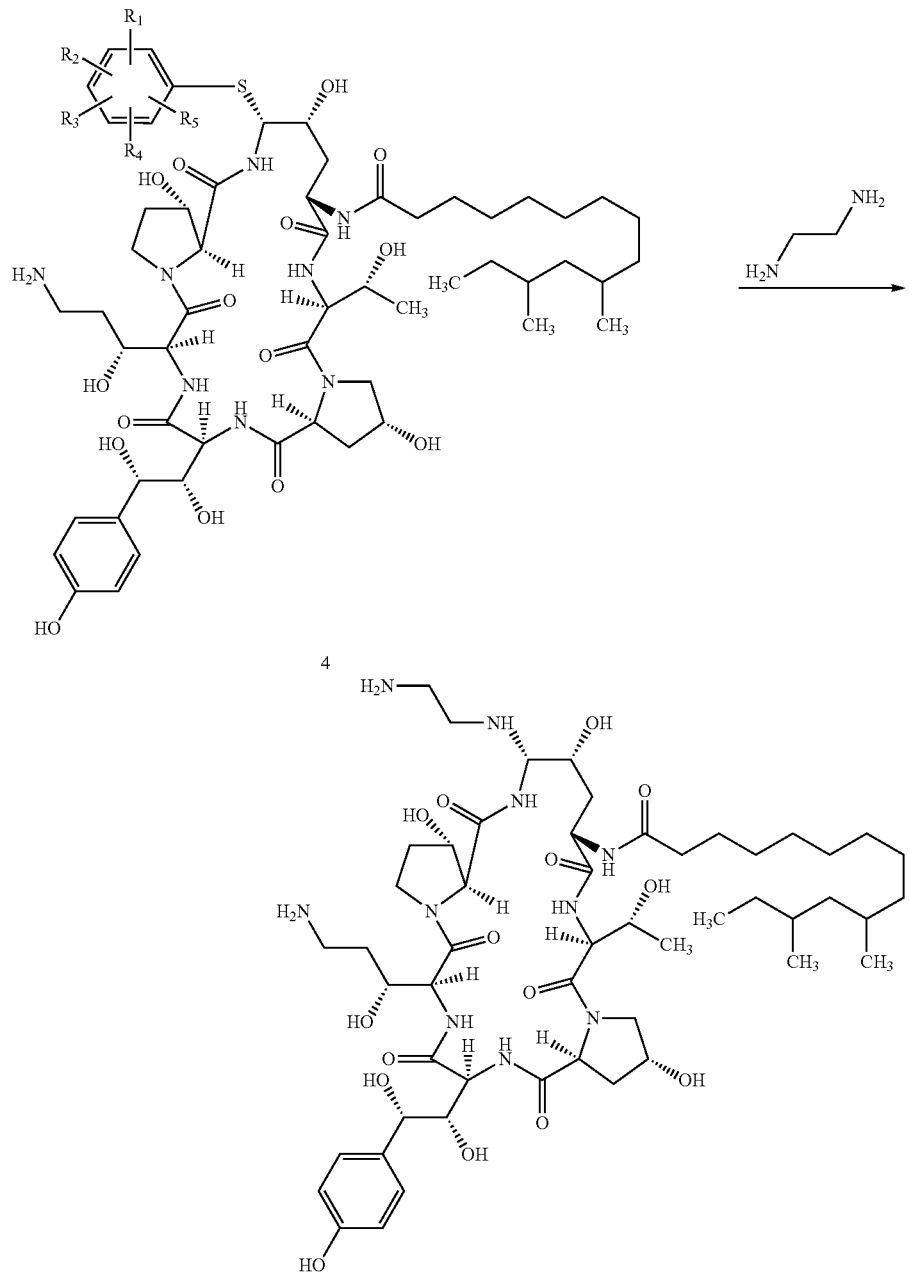

The compound of Formula 3, itself, can also be used to efficiently treat fungus infections, treat and prevent the infection caused by *Candida* and *Aspergillus*, or prepare the medicaments for treating or preventing infectious diseases.

Therefore, a pharmaceutical composition can be provided by the invention, the composition comprising the compound of Formula 3 and pharmaceutically acceptable carriers.

As used herein, the term "efficient amount" refers to the carriers for the administration of therapeutics, including various excipients and diluents. The term refers to the carriers for therapeutics which themselves are not necessary active components and do not produce undue toxicity upon administration. Suitable carriers are well-known to a person skilled in the art. The detailed discussion about pharmaceutically acceptable excipients can be found in Remington's Pharmaceutical Sciences (Mack Pub. Co., N.J., 1991). The pharmaceutically acceptable excipient in a composition includes liquid, for example water, saline, glycerol and ethanol. Additionally, auxiliary agents, such as disintegrant, wetting agent, emulsifier, pH buffering agent, can be present in the carriers.

The pharmaceutical composition can be prepared into various dosage forms according to the different administration routes. The dosage form can be administrated through the following modes: oral, spray, rectum, nose, buccal, local, parenteral, such as subcutaneous, intravenous, intramuscle, intramuscular, intraperitoneal, intrathecal, intraventricular, intrasternum and intracranial injection or infusion, or by means of an explant depot.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The main advantages of the invention include:

1. A new caspofungin analog or the pharmaceutically acceptable salts thereof is provided in the present invention.

2. A new method for preparing caspofungin is provided in the present invention.

3. The method has many advantages, such as short synthesis route, mild reaction condition, simple post-treatment, and increased yield. Additionally, thiophenol with odor and high toxicity is not necessary, thereby not polluting the environment or harming the operators, and the difficulty for operation and the requirement to the equipments are reduced, thereby significantly reducing the cost.

4. In the new preparation method for caspofungin analog provided by the invention, the compound of Formula 2 obtained by fermentation is used as the starting material, and the intermediates produced in the synthesis steps are stable, therefore, the quality of the final product can be controlled, thereby facilitating the industrialization.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

EXAMPLE 1

Preparation of the Compound of Formula 3a from the Compound of Formula 2

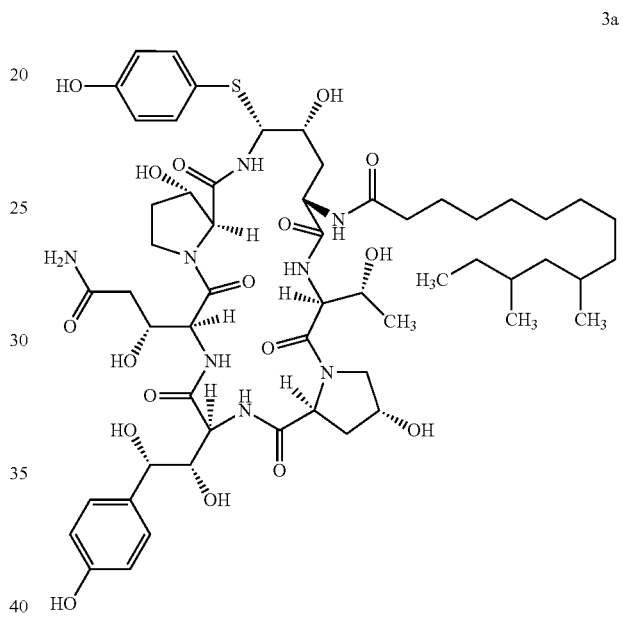

3a

Under $N_2$, acetonitrile (150 ml), the compound of Formula 2 (5.0 g), phenyl boronic acid (0.60 g) and 4-hydroxy thiophenol (1.81 g) were mixed homogeneously. The reaction temperature was reduced to −20 to −15° C. Triflic acid (1.25 ml, 14.13 mmol) was added dropwise. Upon addition, the reaction was conducted at −20 to −15° C. for about 2.5 h. The reaction was monitored by TLC. Upon completion, the reaction was quenched, and aqueous NaOAc (1.15 g NaOAc dissolved in 25 ml of water) was slowly added. Upon addition, the reaction temperature was increased to 20° C., and stirred for 2 h. Great amount of solid was precipitated, and the temperature was reduced to below 0° C. The reaction mixture was filtrated. The filter cake was washed with 60 ml of acetonitrile/water=9:1 (V/V) for 3 times and dried under vacuum for 5 h to obtain the compound of Formula 3a (4.76 g, yield 95.2%). (the yield was calculated based on the weight).

MS (ESI) 1173.6 (M+H$^+$), 1195.6 (M+Na$^+$);

$^1$H-NMR (500.13 MHz, CD$_3$OD) δ 7.35-7.45 (m, 2H), 7.05-7.15 (m, 2H), 6.7-6.8 (m, 4H), 5.38 (s, 1H), 5.05 (d, 1H), 4.94 (d, 1H), 4.57 (dd, 1H), 4.42-4.27 (m, 9H), 3.89 (m, 3H), 3.72 (m, 2H), 2.76 (dd, 1H), 2.45 (dd, 1H), 2.40 (m, 1H), 2.15-2.05 (m, 6H), 1.99 (m, 1H), 1.54 (m, 2H), 1.30-1.20 (m,

15H), 1.10 (d, 3H), 1.10-1.08 (m, 2H), 0.91 (t, 1H), 0.85-0.87 (t, 3H), 0.84, (d, 3H), 0.83 (d, 3H).

EXAMPLE 2

Preparation of the Compound of Formula 4a from the Compound of Formula 3a

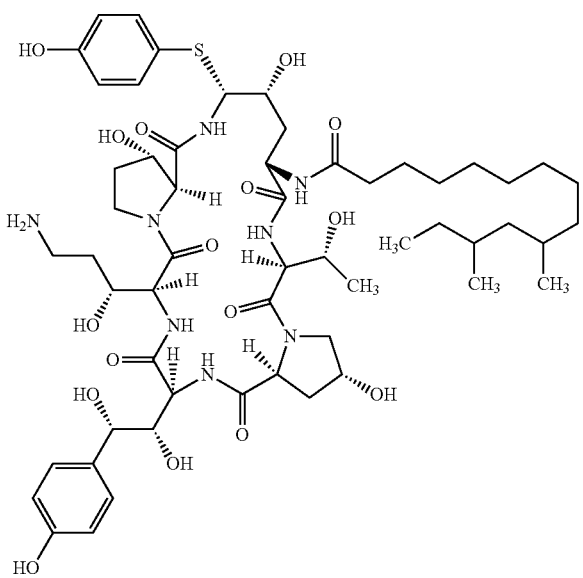

4a

Under $N_2$, the compound of Formula 3a (2.0 g), phenyl boronic acid (0.28 g), tetrahydrofuran (80 ml) were refluxed for 30 min. The reaction mixture was cooled to room temperature, and BSTFA (2.12 ml) was added and stirred for 1 h at room temperature. The reaction mixture was cooled to −10 to −5° C., and the complex of borane and dimethyl sulfide (0.8 ml, 0.94%) was added dropwise. Upon addition, the reaction mixture was warmed to 10 to 15° C., and the reaction was conducted for 3.5 h. The conversion rate for the reaction was 85% monitored by HPLC. Afterwards, 2 N hydrochloric acid (4.8 ml) was added dropwise, and water (160 ml) was added. Upon addition, the reaction mixture was stirred for 24 h at room temperature. The reaction was diluted with water, and loaded onto a preparative column. The column was eluted with 25% acetonitrile/water (0.15% acetic acid). The collections rich in the product were pooled, diluted with water for 1.5 times and loaded onto a preparative column. The column was eluted with 90% acetonitrile/water (0.15% acetic acid), and effluents were collected and concentrated to dryness under reduced pressure to obtain the crude compound of Formula 4a. To the compound, methanol (8 ml) was added and stirred for dissolving the compound. Ethyl acetate (24 ml) was added dropwise at room temperature, and the mixture was stirred for 2 h at room temperature. The solution was cooled and filtered, and the resulting solid was dried to obtain the compound of Formula 4a (1.60 g, yield 80%).

MS (ESI) 1159.6 (M+H$^+$), 1181.6 (M+Na$^+$);

$^1$H-NMR (500.13 MHz, CD$_3$OD) δ 7.35-7.45 (m, 2H), 7.05-7.15 (m, 2H), 6.7-6.8 (m, 4H), 5.38 (s, 1H), 5.05 (d, 1H), 4.94 (d, 1H), 4.57 (dd, 1H), 4.42-4.27 (m, 9H), 3.89 (m, 3H), 3.72 (m, 2H), 2.76 (dd, 1H), 2.65 (m, 2H), 2.45 (m, 2H), 2.15-2.05 (m, 6H), 1.99 (m, 1H), 1.54 (m, 2H), 1.30-1.20 (m, 15H), 1.10 (d, 3H), 1.10-1.08 (m, 2H), 0.91 (t, 1H), 0.85-0.87 (t, 3H), 0.84, (d, 3H), 0.83 (d, 3H).

EXAMPLE 3

Preparation of the Compound of Formula 1 from the Compound of Formula 4a

Under $N_2$, the compound of Formula 4a (1.0 g) was dissolved in methanol (4.2 ml), and the temperature of the solution was reduced to −20 to −15° C. Ethylenediamine (4.2 ml) was added dropwise. Upon addition, the temperature was increased to 30 to 35° C., and the reaction was conducted for 48 h. The conversion rate for the reaction was 99% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 1 (0.93 g, the purity=99.0% by HPLC) in white solid. Afterwards, the compound was dissolved into ethanol (3 ml) and 6% aqueous acetic acid (0.3 ml), and then ethyl acetate (5.3 ml) was added dropwise. The mixture was stirred for 1 h at 10° C., and filtered, and the obtained solid was dried to obtain caspofungin diacetate (the compound of Formula 1) (0.90 g, yield 90%).

MS (ESI): 1093.6 (M+H$^+$);

$^1$H-NMR (500.13 MHz, CD$_3$OD) δ 7.12 (m, 2H), 6.75 (m, 2H), 4.97 (d, 1H), 4.91 (d, 1H), 4.66 (d, 1H), 4.60 (dd, 3.2, 1H), 4.56-4.51 (m, 2H), 4.48 (dd, 1H), 4.32-4.28 (m, 3H) 4.22 (dd, 1H), 4.18 (d, 1H), 4.08-3.96 (m, 3H), 3.83 (m, 1H), 3.76 (d, 1H), 3.05 (t, 2H), 3.02-2.76 (m, 4H), 2.41 (dd, 1H), 2.29-2.17 (m, 3H) 2.11-1.78 (m, 5H), 1.90 (s, 6H), 1.58 (m, 2H), 1.53-1.19 (m, 15H), 1.16 (d, 3H), 1.13-1.00 (m, 2H), 0.91 (m, 1H), 0.87 (t, 3H), 0.85 (degenerated, 6H);

$^{13}$C-NMR (125 MHz, CD$_3$OD) 180.7, 176.7, 174.6, 171.1, 174.0, 173.3, 173.2, 169.4, 159.1, 116.7, 77.8, 76.1, 75.5, 72.5, 71.8, 70.6, 69.8, 64.8, 63.3, 58.9, 58.8, 57.6, 56.7, 56.5, 51.6, 47.5, 46.4, 44.5, 40.9, 39.5, 38.8, 38.5, 37.4, 36.2, 35.1, 33.4, 31.7, 31.6, 31.4, 31.3, 31.1, 30.84, 30.81, 28.5, 27.5, 24.8.

EXAMPLE 4

Preparation of the Compound of Formula 3b from the Compound of Formula 2

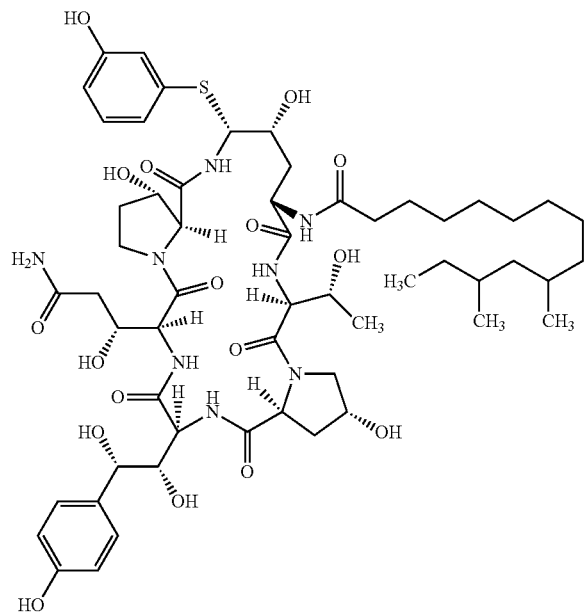

Under $N_2$, acetonitrile (100 ml), the compound of Formula 2 (5.0 g), phenyl boronic acid (0.90 g) and 3-hydroxy thiophenol (1.80 g) were mixed homogeneously. The reaction temperature was reduced to −50 to −45° C. Triflic acid (1.05 ml) was added dropwise. Upon addition, the reaction was conducted at −50 to −45° C. for about 2.5 h. The reaction was monitored by TLC. Upon completion, the reaction was quenched, and aqueous NaOAc (1.15 g NaOAc dissolved in 25 ml of water) was slowly added. Upon addition, the reaction temperature was increased to 20° C., and stirred for 2 h. Great amount of solid was precipitated, and the temperature was reduced to below 0° C. The reaction mixture was filtrated. The filter cake was washed with 60 ml of acetonitrile/water=9:1 (V/V) for 3 times and dried under vacuum for 5 h to obtain the compound of Formula 3b (4.65 g, yield 93%).

MS (ESI) 1173.6 (M+H$^+$), 1195.6 (M+Na$^+$);

$^1$H-NMR (500.13 MHz, CD$_3$OD) δ7.1-7.20 (m, 3H), 6.7-6.9 (m, 5H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.76 (dd, 1H), 2.45 (dd, 1H), 2.40 (m, 1H), 2.15-2.05 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.85-0.87 (t, 3H), 0.84, (d, 3H), 0.83 (d, 3H);

EXAMPLE 5

Preparation of the Compound of Formula 4b from the Compound of Formula 3b

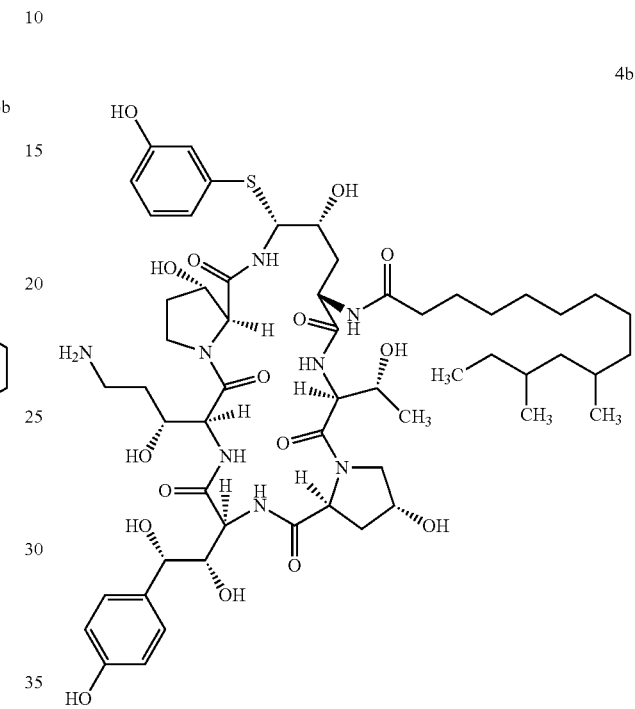

Under $N_2$, the compound of Formula 3b (2.0 g), phenyl boronic acid (0.50 g), tetrahydrofuran (100 ml) were refluxed for 30 min. The reaction mixture was cooled to room temperature, and BSTFA (2.12 ml) was added and stirred for 1 h at room temperature. The reaction mixture was cooled to −20 to −15° C., and the complex of tetrahydrofuran in tetrahydrofuran (13.6 ml, 1 M) was added dropwise. Upon addition, the reaction was conducted for 3.5 h at −20 to −15° C. The conversion rate for the reaction was 85% monitored by HPLC. Afterwards, 2 N hydrochloric acid (4.8 ml) was added dropwise, and water (160 ml) was added. Upon addition, the reaction mixture was stirred for 24 h at room temperature. The reaction was diluted with water, and loaded onto a preparative column. The column was eluted with 25% acetonitrile/water (0.15% acetic acid). The collections rich in the product were pooled, diluted with water for 1.5 times and loaded onto a preparative column. The column was eluted with 90% acetonitrile/water (0.15% acetic acid), and effluents were collected and concentrated to dryness under reduced pressure to obtain the crude compound of Formula 4b. To the compound, methanol (8 ml) was added and stirred for dissolving the compound. Ethyl acetate (24 ml) was added dropwise at room temperature, and the mixture was stirred for 2 h at room temperature. The solution was cooled and filtered, and the resulting solid was dried to obtain the compound of Formula 4b (1.60 g, yield 80%).

MS (ESI) 1159.6 (M+H$^+$), 1181.6 (M+Na$^+$);

$^1$H-NMR (500.13 MHz, CD$_3$OD) δ 7.1-7.20 (m, 3H), 6.7-6.9 (m, 5H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.76 (dd,

1H), 2.60 (m, 2H), 2.43 (m, 2H), 2.15-2.05 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.85-0.87 (t, 3H), 0.84, (d, 3H), 0.83 (d, 3H);

EXAMPLE 6

Preparation of the Compound of Formula 1 from the Compound of Formula 4b

Under $N_2$, the compound of Formula 4b (1.0 g) was dissolved in tetrahydrofuran (6 ml), and the temperature of the solution was reduced to 0 to 5° C. Ethylenediamine (4.2 ml) was added dropwise. Upon addition, the temperature was increased to room temperature, and the reaction was conducted for 24 h. The conversion rate for the reaction was 99% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 1 (0.92 g, 92%, the purity=99.0% by HPLC) in white solid. Afterwards, the compound was dissolved into ethanol (3 ml) and 6% aqueous acetic acid (0.3 ml), and then ethyl acetate (5.3 ml) was added dropwise. The mixture was stirred for 1 h at 10° C., and filtered, and the obtained solid was dried to obtain caspofungin diacetate (the compound of Formula 1) (0.88 g, yield 88%).

EXAMPLE 7

Preparation of the Compound of Formula 3c from the Compound of Formula 2

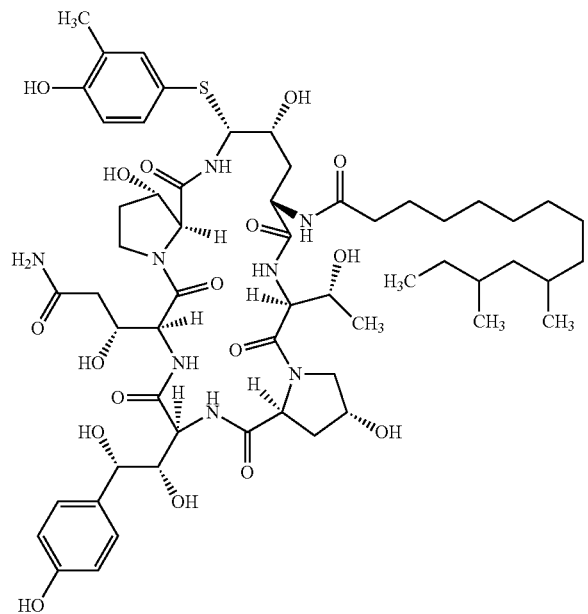

3c

Under $N_2$, acetonitrile (200 ml), the compound of Formula 2 (5.0 g), phenyl boronic acid (1.50 g) and 4-hydroxy-3-methyl thiophenol (2.05 g) were mixed homogeneously. The reaction temperature was reduced to below −15° C. Methanesulfonic acid (1.36 g) was slowly added. Upon addition, the reaction temperature was increased to 35 to 40° C., and the reaction was conducted for about 2.5 h. The reaction was monitored by TLC. Upon completion, the reaction was quenched, and aqueous NaOAc (1.20 g NaOAc dissolved in 20 ml of water) was slowly added. Upon addition, the reaction temperature was increased to 20° C., and the solution was stirred for 2 h. Great amount of solid was precipitated, and the temperature was reduced to below 0° C. The reaction mixture was filtrated. The filter cake was washed with 50 ml of acetonitrile/water=9:1 (V/V) for 3 times and dried under vacuum for 5 h to obtain the compound of Formula 3c (4.60 g, yield 92%).

MS (ESI) 1187.6 (M+H$^+$);
$^1$H-NMR (500.13 MHz, CD$_3$OD) δ7.15-7.20 (m, 3H), 7.0-6.9 (m, 1H), 6.6-6.7 (m, 3H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.75 (dd, 1H), 2.45 (dd, 1H), 2.40 (m, 1H), 2.20 (s, 3H), 2.15-2.06 (m, 6H), 1.97 (m, 1H), 1.54 (m, 2H), 1.30-1.20 (m, 15H), 1.10 (d, 3H), 1.10-1.08 (m, 2H), 0.91 (t, 1H), 0.85-0.88 (t, 3H), 0.84, (d, 3H), 0.83 (d, 3H);

EXAMPLE 8

Preparation of the Compound of Formula 4c from the Compound of Formula 3c

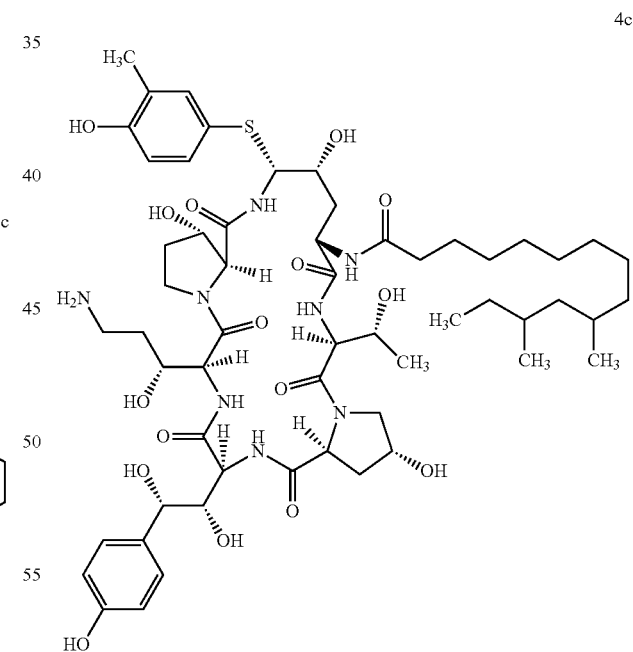

4c

Under $N_2$, the compound of Formula 3c (2.0 g), phenyl boronic acid (0.48 g), tetrahydrofuran (60 ml) were refluxed for 30 min. The reaction mixture was cooled to room temperature, BSTFA (2.40 ml) was added and the resulting reaction mixture was stirred for 1 h at room temperature. The reaction mixture was maintained at 15 to 20° C., and the solution of borane in dimethyl sulfide (1.4 ml, 0.94%) was added dropwise. Upon addition, the reaction was conducted for 3.5 h at 15 to 20° C. The conversion rate for the reaction was 86% monitored by HPLC. Afterwards, 2 N hydrochloric acid (4.8 ml) was added dropwise, and water (160 ml) was added. Upon addition, the reaction mixture was stirred for 24 h at room temperature. The reaction was diluted with water, and loaded onto a preparative column. The column was eluted with 25% acetonitrile/water (0.15% acetic acid). The collections rich in the product were pooled, diluted with water for 1.5 times and loaded onto a preparative column. The column was eluted with 90% acetonitrile/water (0.15% acetic acid), and effluents were collected and concentrated to dryness under reduced pressure to obtain the crude compound of Formula 4c. To the compound, methanol (8 ml) was added and stirred for dissolving the compound. Ethyl acetate (24 ml) was added dropwise at room temperature, and the mixture was stirred for 2 h at room temperature. The solution was cooled and filtered, and the resulting solid was dried to obtain the compound of Formula 4c (1.60 g, yield 80%).

MS (ESI) 1173.6 (M+H$^+$);

$^1$H-NMR (500.13 MHz, CD$_3$OD) δ7.15-7.20 (m, 3H), 7.0-6.9 (m, 1H), 6.6-6.7 (m, 3H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.75 (dd, 1H), 2.66 (m, 2H), 2.42 (m, 2H), 2.20 (s, 3H), 2.15-2.06 (m, 6H), 1.97 (m, 1H), 1.54 (m, 2H), 1.30-1.20 (m, 15H), 1.10 (d, 3H), 1.10-1.08 (m, 2H), 0.91 (t, 1H), 0.85-0.88 (t, 3H), 0.84, (d, 3H), 0.83 (d, 3H);

EXAMPLE 9

Preparation of the Compound of Formula 1 from the Compound of Formula 4c

Under N$_2$, the compound of Formula 4c (1.0 g) was dissolved in ethanol (5 ml). Ethylenediamine (4.5 ml) was added dropwise at 35 to 40° C. Upon addition, the reaction was conducted for 24 h at 35 to 40° C. The conversion rate for the reaction was 99% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 1 (0.82 g, 82%, the purity=99.0% by HPLC) in white solid. Afterwards, the compound was dissolved into ethanol (3 ml) and 6% aqueous acetic acid (0.3 ml), and then ethyl acetate (5.3 ml) was added dropwise. The mixture was stirred for 1 h at 10° C., and filtered, and the obtained solid was dried to obtain caspofungin diacetate (the compound of Formula 1) (0.70 g, yield 70%).

EXAMPLE 10

Preparation of the Compound of Formula 3d from the Compound of Formula 2

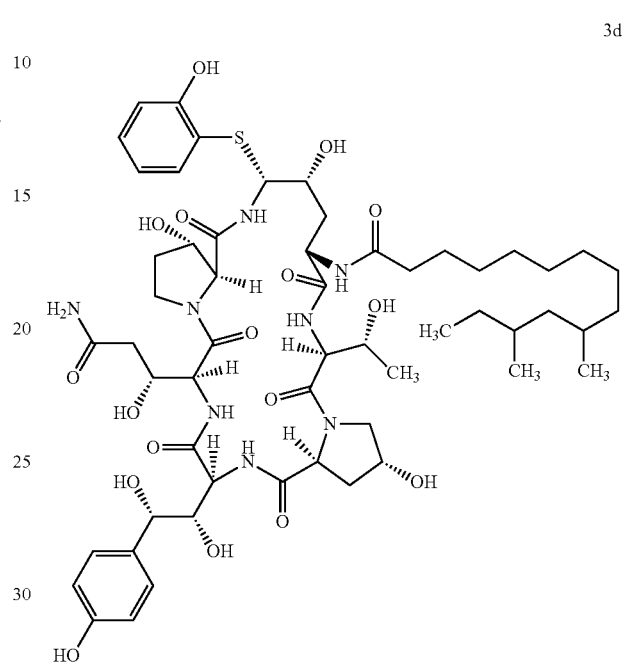

3d

Under N$_2$, acetonitrile (20 ml), the compound of Formula 2 (1.0 g), phenyl boronic acid (0.12 g) and 2-hydroxy thiophenol (0.35 g) were mixed homogeneously. The reaction temperature was increased to 35 to 45° C. Triflic acid (0.35 ml) was added dropwise. Upon addition, the reaction was conducted for about 2.5 h at 35 to 45° C. The reaction was monitored by TLC. Upon completion, the reaction was quenched, and aqueous NaOAc (0.23 g NaOAc dissolved in 5 ml of water) was slowly added. Upon addition, the reaction temperature was increased to 20° C., and the solution was stirred for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 4 h to obtain the compound of Formula 3d (0.96 g).

MS (ESI) 1173.6 (M+H$^+$), 1195.6 (M+Na$^+$);

$^1$H-NMR (500.13 MHz, CD$_3$OD) δ7.1-7.20 (m, 3H), 7.0-6.9 (m, 2H), 6.65-6.9 (m, 3H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.75 (dd, 1H), 2.45 (dd, 1H), 2.40 (m, 1H), 2.15-2.06 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.85-0.87 (t, 3H), 0.84, (d, 3H), 0.83 (d, 3H);

EXAMPLE 11

Preparation of the Compound of Formula 4d from the Compound of Formula 3d

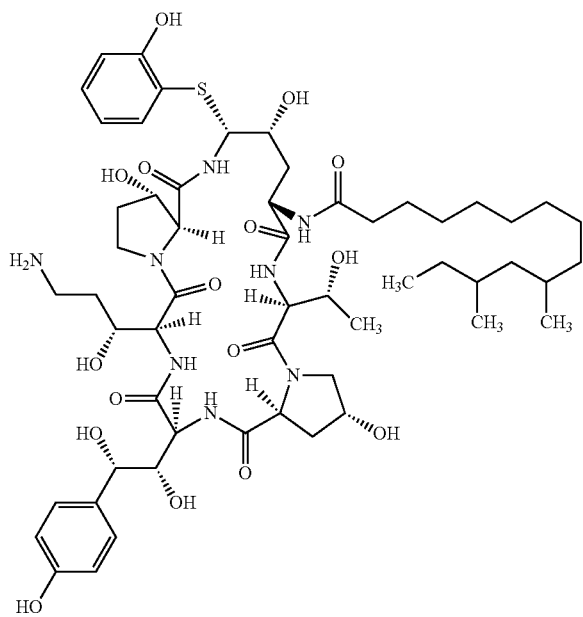

4d

Under $N_2$, the compound of Formula 3d (2.0 g), phenyl boronic acid (0.62 g), tetrahydrofuran (80 ml) were refluxed for 30 min. The reaction mixture was cooled to room temperature, BSTFA (2.80 ml) was added and the resulting reaction mixture was stirred for 1 h at room temperature. The reaction mixture was cooled to below −20 to −15° C., and the borane solution in dimethyl sulfide (1.8 ml, 0.94%) was added dropwise. Upon addition, the reaction temperature was increased to 10 to 15° C., and the reaction was conducted for 3.5 h. The conversion rate for the reaction was 88% monitored by HPLC. Afterwards, 2 N hydrochloric acid (4.8 ml) was added dropwise, and water (160 ml) was added. Upon addition, the reaction mixture was stirred for 24 h at room temperature. The reaction was diluted with water, and loaded onto a preparative column. The column was eluted with 25% acetonitrile/water (0.15% acetic acid). The collections rich in the product were pooled, diluted with water for 1.5 times and loaded onto a preparative column. The column was eluted with 90% acetonitrile/water (0.15% acetic acid), and effluents were collected and concentrated to dryness under reduced pressure to obtain the crude compound of Formula 4d. To the compound, methanol (8 ml) was added and stirred for dissolving the compound. Ethyl acetate (24 ml) was added dropwise at room temperature, and the resulting solution was stirred for 2 h at room temperature. The solution was cooled and filtered, and the resulting solid was dried to obtain the compound of Formula 4d (1.70 g, yield 85%).

MS (ESI) 1159.6 (M+H$^+$), 1181.6 (M+Na$^+$);

$^1$H-NMR (500.13 MHz, CD$_3$OD) δ7.1-7.20 (m, 3H), 7.0-6.9 (m, 21-1), 6.65-6.9 (m, 3H), 5.38 (s, 1H), 5.05 (d, 1H), 4.94 (d, 1H), 4.57 (dd, 1H), 4.42-4.28 (m, 9H), 3.89 (m, 3H), 3.72 (m, 2H), 2.75 (dd, 1H), 2.63 (m, 1H), 2.45 (m, 2H), 2.15-2.06 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.85-0.87 (t, 3H), 0.84, (d, 3H), 0.83 (d, 3H);

EXAMPLE 12

Preparation of the Compound of Formula 1 from the Compound of Formula 4d

Under $N_2$, the compound of Formula 4d (1.0 g) was dissolved in ethanol (4.5 ml), the resulting solution was cooled to −20 to −15° C. Ethylenediamine (4.5 ml) was added dropwise. Upon addition, the reaction temperature was increased to 0 to 5° C., and the reaction was conducted for 96 h. The conversion rate for the reaction was 98% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 1 (0.89 g, 89%, the purity=97.0% by HPLC) in white solid. Afterwards, the compound was dissolved into ethanol (3 ml) and 6% aqueous acetic acid (0.3 ml), and then ethyl acetate (7.3 ml) was added dropwise. The mixture was stirred for 1 h at 10° C., and filtered, and the obtained solid was dried to obtain caspofungin diacetate (the compound of Formula 1) (0.82 g, yield 82%).

EXAMPLE 13

Preparation of the Compound of Formula 3e from the Compound of Formula 2

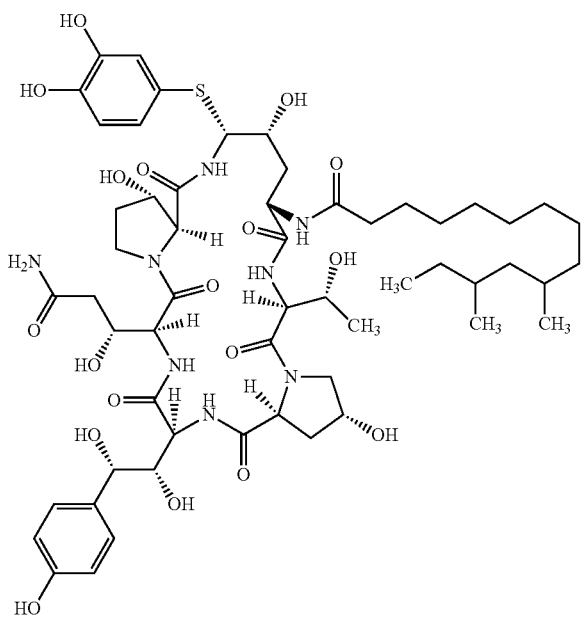 [SMILES: CCC(C)CC(C)CCCCCCCCC(=O)N[C@H]1C[C@@H](O)[C@@H](Sc2ccc(O)cc2)NC(=O)[C@@H]2[C@@H](O)CCN2C(=O)[C@H]([C@H](O)CC(N)=O)NC(=O)[C@H]([C@H](O)[C@@H](O)c2ccc(O)cc2)NC(=O)[C@@H]2C[C@@H](O)CN2C(=O)[C@H]([C@@H](C)O)NC1=O]

3e

Under $N_2$, acetonitrile (30 ml), the compound of Formula 2 (1.0 g), phenyl boronic acid (0.23 g) and 3,4-dihydroxy thiophenol (0.42 g) were mixed homogeneously. The reaction temperature was reduced to below −50 to −45° C. Triflic acid (0.25 ml) was added dropwise. Upon addition, the reaction was conducted for about 2.5 h at −50 to −45° C. The reaction was monitored by TLC. Upon completion, the reaction was quenched, and aqueous NaOAc (0.23 g NaOAc dissolved in 3.5 ml of water) was slowly added. Upon addition, the reaction temperature was increased to 20° C., and the solution was stirred for 2 h. Great amount of solid was precipitated, and the temperature was reduced to below 0° C. The reaction mixture was filtrated. The filter cake was washed with 12.5 ml of acetonitrile/water=9:1 (V/V) for 3 times and dried under vacuum for 5 h to obtain the compound of Formula 3e (0.82 g, yield 87%).

MS (ESI) 1189.6 (M+H$^+$); 1211.6 (M+Na$^+$);

$^1$H-NMR (500.13 MHz, CD$_3$OD) δ7.15-7.20 (m, 2H), 6.6-6.75 (m, 4H), 6.45 (m, 1H), 5.38 (s, 1H), 5.06 (d, 1H), 4.94 (d, 1H), 4.57 (dd, 1H), 4.42-4.28 (m, 9H), 3.89 (m, 3H), 3.72 (m, 2H), 2.75 (dd, 1H), 2.45 (dd, 1H), 2.40 (m, 1H), 2.15-2.06 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.85-0.88 (t, 3H), 0.84, (d, 3H), 0.83 (d, 3H);

EXAMPLE 14

Preparation of the Compound of Formula 4e from the Compound of Formula 3e

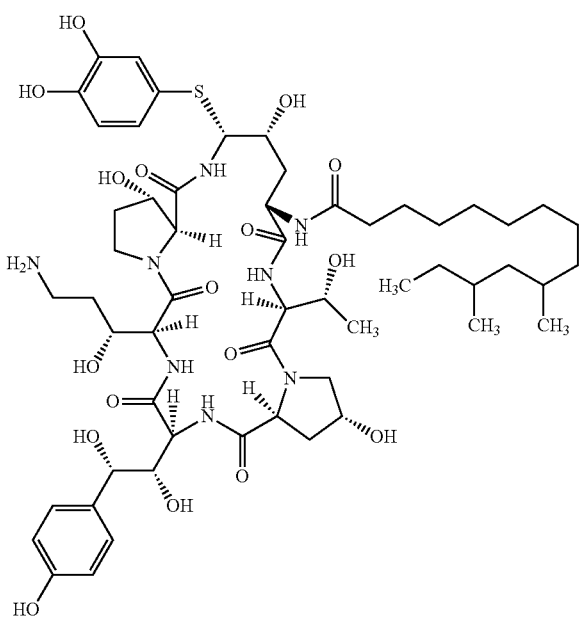 [SMILES: CCC(C)CC(C)CCCCCCCCC(=O)N[C@H]1C[C@@H](O)[C@@H](Sc2ccc(O)cc2)NC(=O)[C@@H]2[C@@H](O)CCN2C(=O)[C@H]([C@H](O)CCN)NC(=O)[C@H]([C@H](O)[C@@H](O)c2ccc(O)cc2)NC(=O)[C@@H]2C[C@@H](O)CN2C(=O)[C@H]([C@@H](C)O)NC1=O]

4e

Under N$_2$, the compound of Formula 3e (2.0 g), phenyl boronic acid (0.62 g), tetrahydrofuran (60 ml) were refluxed for 30 min. The reaction mixture was cooled to room temperature, BSTFA (2.80 ml) was added and the resulting reaction mixture was stirred for 1 h at room temperature. The reaction mixture was cooled to −5 to 0° C., and the borane solution in dimethyl sulfide (1.7 ml) was added dropwise. Upon addition, the reaction temperature was increased to 10° C., and the reaction was conducted for 3.5 h. The conversion rate for the reaction was 88% monitored by HPLC. Afterwards, 2 N hydrochloric acid (4.8 ml) was added dropwise, and water (160 ml) was added. Upon addition, the reaction mixture was stirred for 24 h at room temperature. The reaction was diluted with water, and loaded onto a preparative column. The column was eluted with 25% acetonitrile/water (0.15% acetic acid). The collections rich in the product were pooled, diluted with water for 1.5 times and loaded onto a preparative column. The column was eluted with 90% acetonitrile/water (0.15% acetic acid), and effluents were collected and concentrated to dryness under reduced pressure to obtain the crude compound of Formula 4e. To the compound, methanol (8 ml) was added and stirred for dissolving the compound. Ethyl acetate (24 ml) was added dropwise at room temperature, and the resulting solution was stirred for 2 h at room temperature. The solution was cooled and filtered, and the resulting solid was dried to obtain the compound of Formula 4e (1.64 g, yield 82%).

MS (ESI) 1175.6 (M+H$^+$); 1196.6 (M+Na$^+$);

$^1$H-NMR (500.13 MHz, CD$_3$OD) δ7.15-7.20 (m, 2H), 6.6-6.75 (m, 4H), 6.45 (m, 1H), 5.38 (s, 1H), 5.06 (d, 1H), 4.94 (d, 1H), 4.57 (dd, 1H), 4.42-4.28 (m, 9H), 3.89 (m, 3H), 3.72 (m, 2H), 2.75 (dd, 1H), 2.64 (m, 2H), 2.45 (m, 2H), 2.40 (m, 1H), 2.15-2.06 (m, 6H), 1.98 (m, 1H), 1.54 (m, 2H), 1.30-1.20 (m, 15H), 1.10 (d, 3H), 1.10-1.08 (m, 2H), 0.91 (t, 1H), 0.85-0.88 (t, 3H), 0.84, (d, 3H), 0.83 (d, 3H);

EXAMPLE 15

Preparation of the Compound of Formula 1 from the Compound of Formula 4e

Under N$_2$, the compound of Formula 4e (1.0 g) was dissolved in methanol (4.5 ml), the resulting solution was cooled to −20 to −15° C. Ethylenediamine (4.5 ml) was added dropwise. Upon addition, the reaction temperature was increased to room temperature, and the reaction was conducted for 72 h. The conversion rate for the reaction was 98% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 1 (0.95 g, 95%, the purity=97.0% by HPLC) in white solid. Afterwards, the compound was dissolved into ethanol (3 ml) and 6% aqueous acetic acid (0.3 ml), and then ethyl acetate (5.3 ml) was added dropwise. The mixture was stirred for 1 h at 10° C., and filtered, and the obtained solid was dried to obtain caspofungin diacetate (the compound of Formula 1) (0.90 g, yield 90%).

EXAMPLE 16

Preparation of the Composition Comprising the Compound of Formula 4a

| Component | Amount |
| --- | --- |
| The compopund of Formula 4a | 42 mg/ml |
| Sucrose | 30 mg/ml |
| Mannitol | 20 mg/ml |

| Component | Amount |
| --- | --- |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 4a was added, wherein the amount of the compound in the resulting solution is 42 mg/ml. The mixed solution was stirred, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

EXAMPLE 17

Preparation of the Composition Comprising the Compound of Formula 4b

| Component | Amount |
| --- | --- |
| The compopund of Formula 4b | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 4b was added, wherein the amount of the compound in the resulting solution is 42 mg/ml. The mixed solution was stirred, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

EXAMPLE 18

Preparation of the Composition Comprising the Compound of Formula 4c

| Component | Amount |
| --- | --- |
| The compopund of Formula 4c | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 4c was added, wherein the amount of the compound in the resulting solution is 42 mg/ml. The mixed solution was stirred, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

EXAMPLE 19

Preparation of the Composition Comprising the Compound of Formula 4d

| Component | Amount |
| --- | --- |
| The compopund of Formula 4d | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 4d was added, wherein the amount of the compound in the resulting solution is 42 mg/ml. The mixed solution was stirred, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

EXAMPLE 20

Preparation of the Composition Comprising the Compound of Formula 4e

| Component | Amount |
| --- | --- |
| The compopund of Formula 4e | 42 mg/ml |
| Sucrose | 30 mg/ml |
| Mannitol | 20 mg/ml |
| Acetic acid | 1.5 mg/ml |
| Sodium hydroxide | 1N aqueous sodium hydroxide |

Into a 25 ml flask, 0.75 g of sucrose, 0.5 g of mannitol, 17.5 ml of water, 0.5 ml of 75 mg/ml aqueous acetic acid were added. And then, the compound of Formula 4e was added, wherein the amount of the compound in the resulting solution is 42 mg/ml. The mixed solution was stirred, and pH of the solution was regulated to 6 by using 1 N aqueous NaOH. The volume of the mixed solution was regulated by using water. Afterwards, the solution was filtered through a sterile filter. The filtrate was transferred into a 10 ml tube with 1.75 ml of filtrate per tube. The tubes were transferred into a freeze dryer, and the solution was lyophilized into a white powder.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. A compound of Formula 4 or the pharmaceutically acceptable salts thereof,

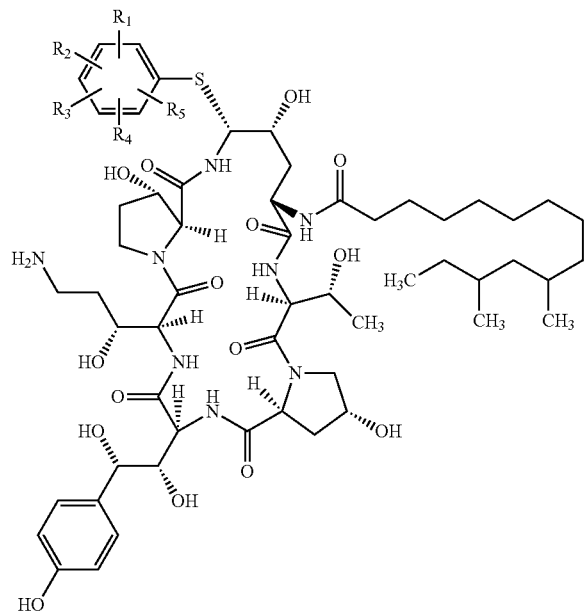

wherein $R_1$ is selected from hydroxy, benzyloxy, phenoxy, substituted phenoxy, or substituted benzyloxy; and $R_2$, $R_3$, $R_4$, and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

2. The compound according to claim 1, wherein $R_1$ is selected from hydroxy, benzyloxy, phenoxy, or substituted phenoxy; and $R_2$, $R_3$, $R_4$, and $R_5$ are selected from hydrogen, C1-C4 alkyl, C1-C4 alkoxy, hydroxyl, bromine or nitro.

3. The compound according to claim 2, wherein $R_1$ is selected from hydroxy; and $R_2$, $R_3$, $R_4$, and $R_5$ are selected from hydrogen, methyl, or hydroxyl.

4. The compound according to claim 3, wherein the compound is the compound of Formula 4a, 4b, 4c, 4d, or 4e:

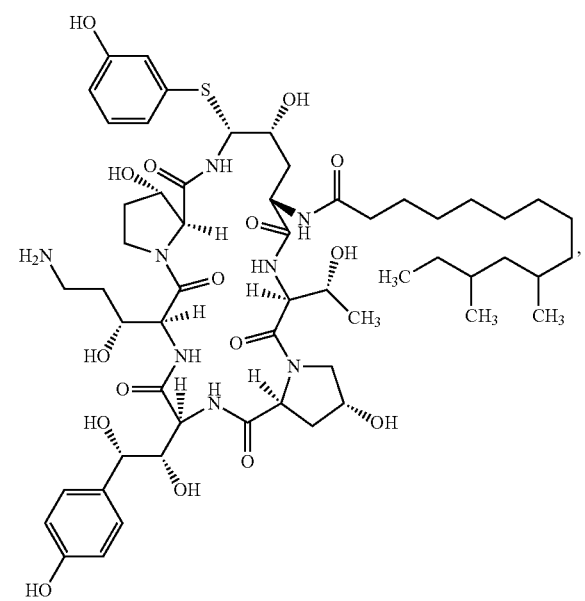

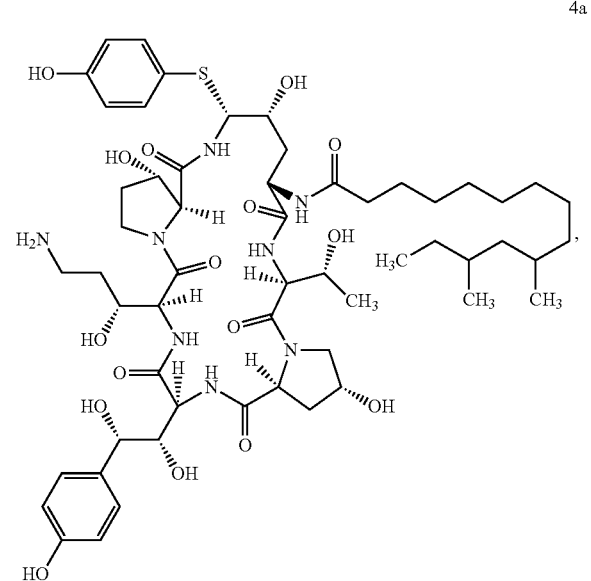

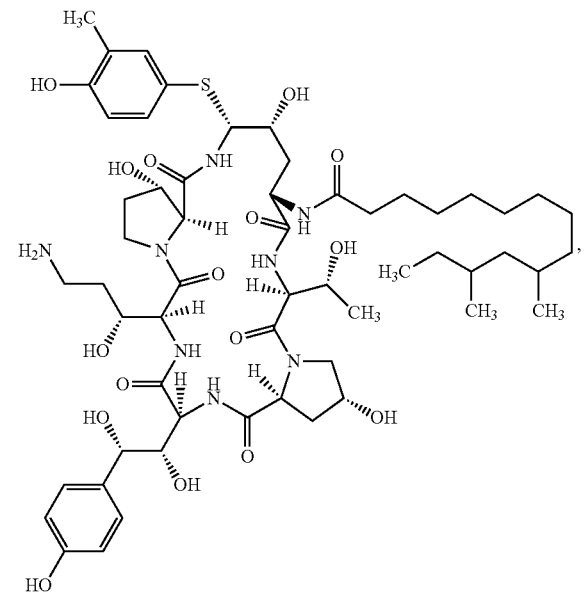

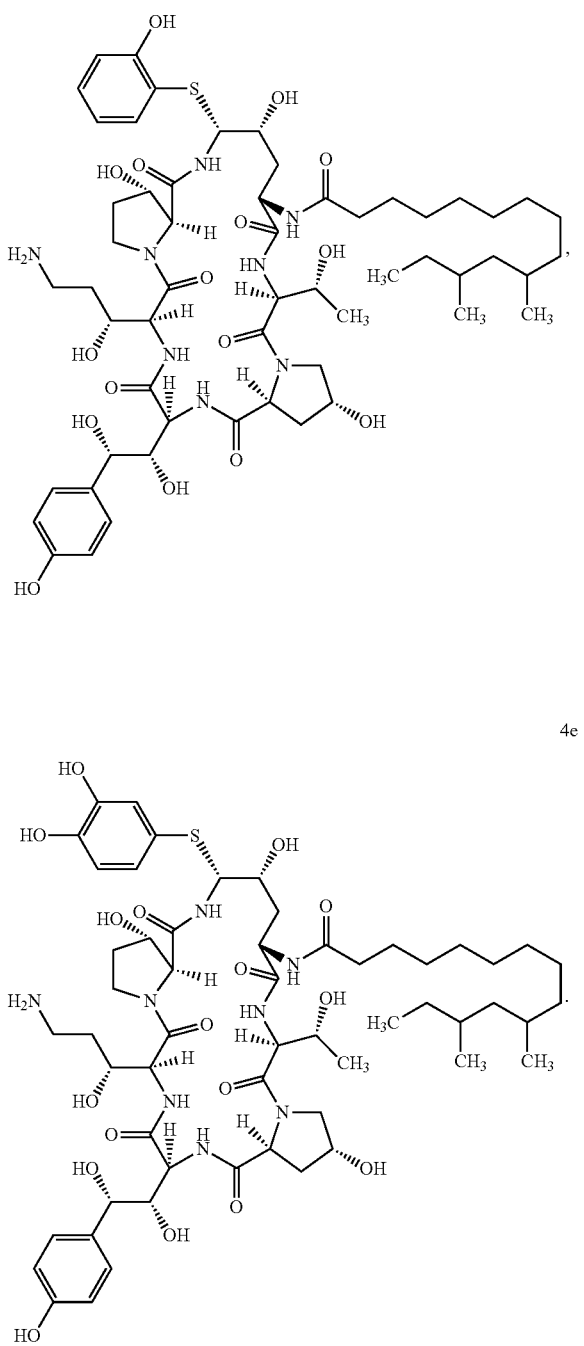

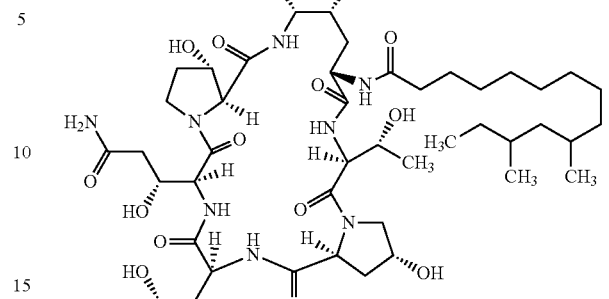

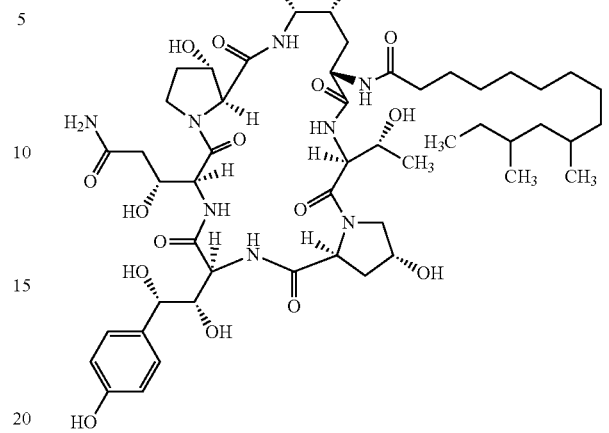

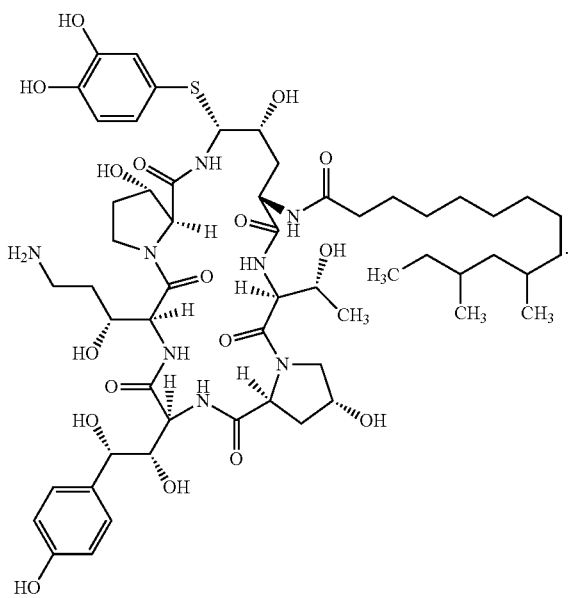

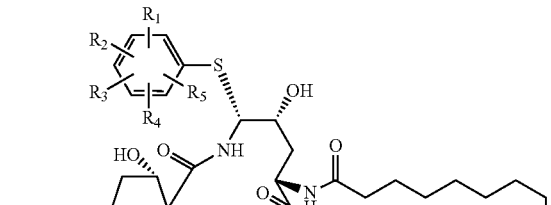

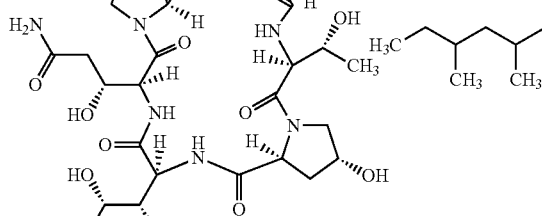

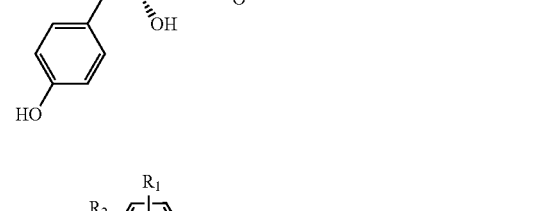

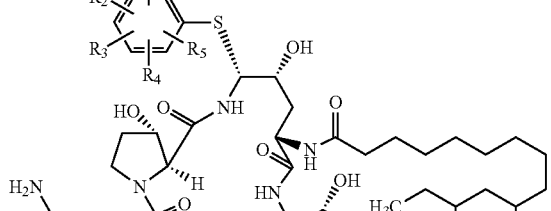

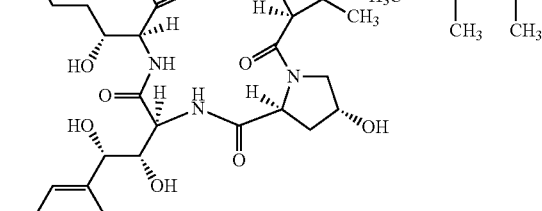

5. The compound according to claim 4, wherein the compound is the compound of Formula 4a.

6. A preparation method for the compound or the pharmaceutically acceptable salts thereof according to claim 1, wherein said method comprises the following steps:

(a) mixing the compound of Formula 2 with strong leaving-group compound 5, thereby obtaining the compound of Formula 3; and (b) mixing the compound of Formula 3 with a hydroxyl protectant, and then with a borane complex to obtain the compound of Formula 4;

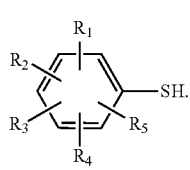

7. The preparation method according to claim 6, wherein, in step (a), in the strong leaving-group compound 5, $R_1$ is selected from hydroxy, benzyloxy, phenoxy, substituted phenoxy, or substituted benzyloxy; and $R_2$, $R_3$, $R_4$, and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

8. The preparation method according to claim 7, wherein the strong leaving-group compound 5 includes a sulphydryl-substituted aromatic ring where $R_1$ is selected from hydroxy, benzyloxy, phenoxy, or substituted phenoxy; and $R_2$, $R_3$, $R_4$, and $R_5$ are selected from hydrogen, C1-C4 alkyl, C1-C4 alkoxy, hydroxyl, bromine or nitro.

9. The preparation method according to claim 8, wherein, in the sulphydryl-substituted aromatic ring, $R_1$ is selected from hydroxy; and $R_2$, $R_3$, $R_4$, and $R_5$ are selected from hydrogen, methyl, or hydroxyl.

10. The preparation method according to claim 9, wherein the sulphydryl-substituted aromatic ring is 4-hydroxy thiophenol.

11. The preparation method according to claim 6, wherein the strong leaving-group compound 5 is mixed with an acid, wherein said acid is selected from trifluoroacetic acid, triflic acid, camphor sulfonic acid, methanesulfonic acid or p-toluene sulphonic acid.

12. The preparation method according to claim 6, wherein the temperature for mixing in step (a) is −50° C. to 40° C.

13. The preparation method according to claim 6, wherein the hydroxyl protectant in step (b) is selected from boric acid protectants or silicane agents.

14. The preparation method according to claim 6, wherein the borane complex in step (b) is selected from: a complex of borane and tetrahydrofuran, borane and dimethyl sulfide, borane and diphenyl sulfide, borane and dibenzyl sulfide, borane and dioxane, borane and 1,4-oxathiane, or a complex of $BH_2Cl$ and dimethyl sulfide.

15. The compound or the pharmaceutically acceptable salts thereof according to claim 1 used for preparing the compound of Formula 1,

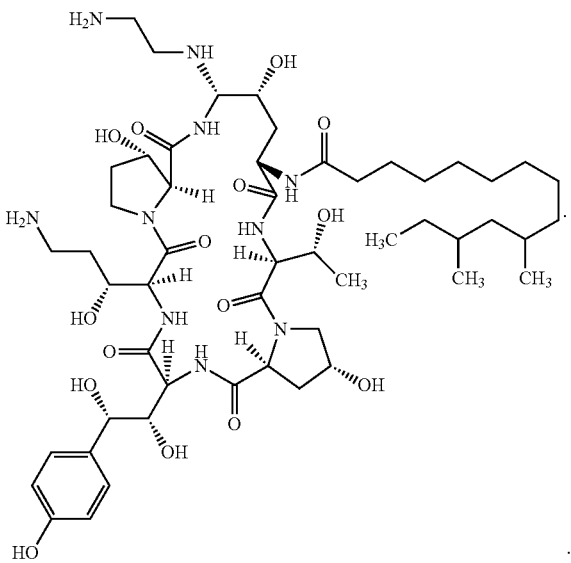

16. A preparation method for a compound of Formula 1, wherein said method comprises the following steps: mixing the compound of Formula 4 with ethylenediamine to obtain the compound of Formula 1,

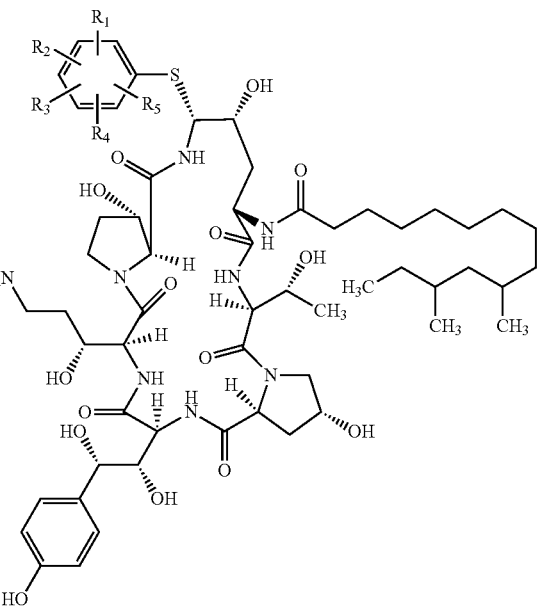

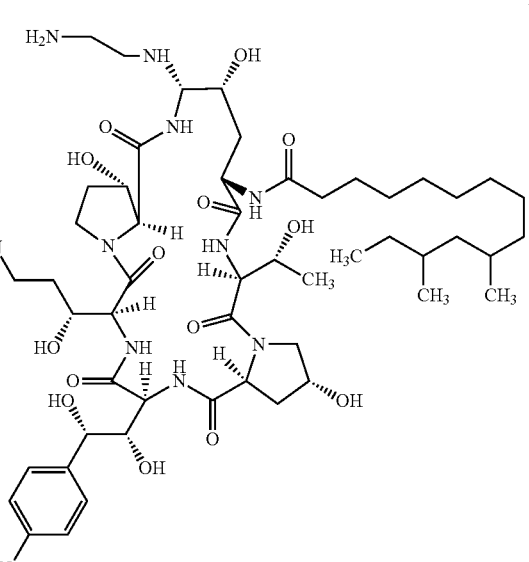

wherein $R_1$ is selected from hydroxy, benzyloxy, phenoxy, substituted phenoxy, or substituted benzyloxy; and $R_2$, $R_3$, $R_4$ and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

17. The preparation method according to claim 16, wherein the compound of Formula 4 is mixed with ethylenediamine dissolved in a solvent selected from the following group: methanol, ethanol, tetrahydrofuran, 2-methyl tetrahydrofuran, isopropanol, trifluoroethanol, acetonitrile or dichloromethane,

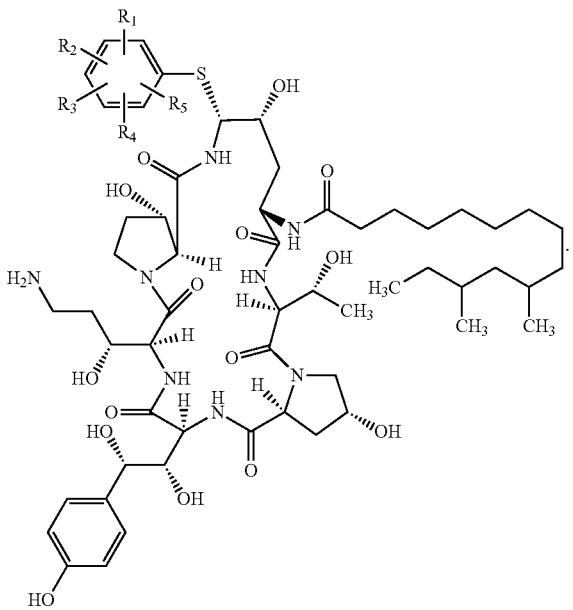

18. The preparation method according to claim 16, wherein the temperature for mixing is 0° C. to 40° C.

19. A preparation method for a compound of Formula 1, wherein said method comprises the following steps:

(a) mixing the compound of Formula 2 with a strong leaving-group compound 5, thereby obtaining the compound of Formula 3;

(b) mixing the compound of Formula 3 with a hydroxyl protectant, and then with a borane complex to obtain the compound of Formula 4; and (c) mixing the compound of Formula 4 with ethylenediamine to obtain the compound of Formula 1,

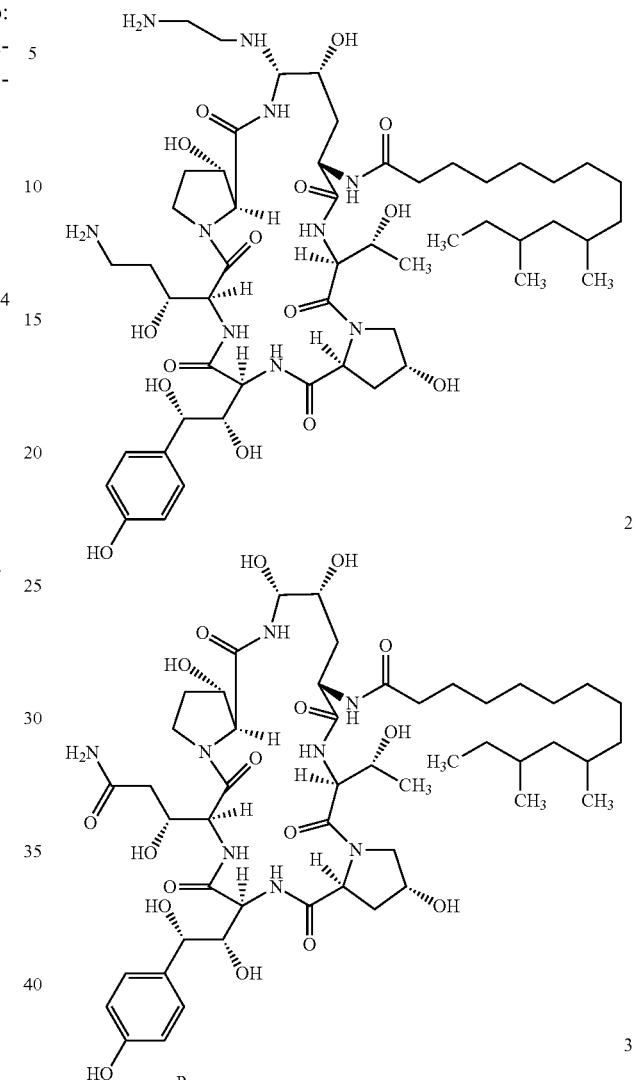

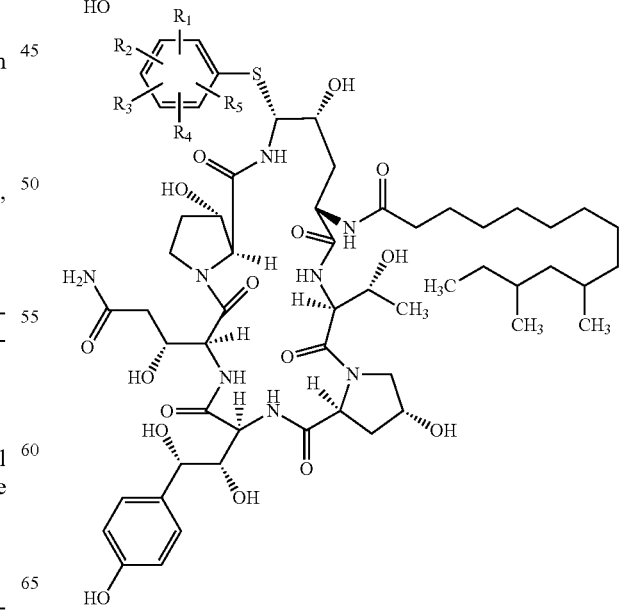

4

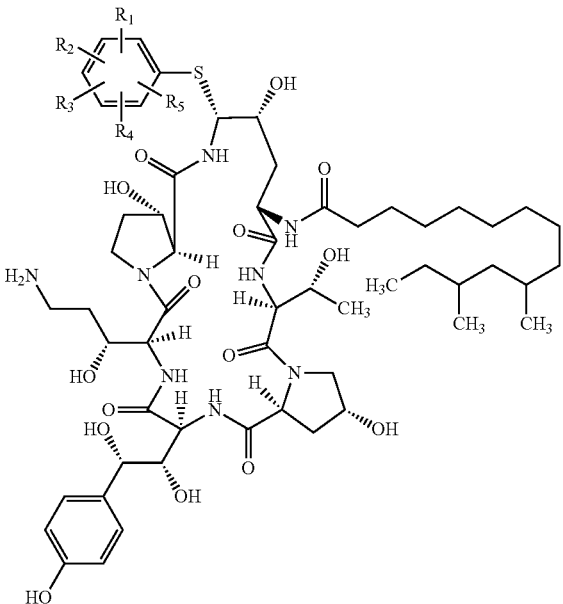

5

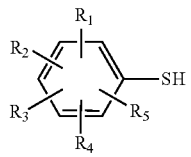

wherein $R_1$ is selected from hydroxy, benzyloxy, phenoxy, substituted phenoxy, or substituted benzyloxy; and $R_2$, $R_3$, $R_4$ and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

20. The preparation method according to claim 6, wherein the temperature for mixing in step (a) is −20° C. to −15° C.

21. The preparation method according to claim 6, wherein the borane complex in step (b) is selected from: a complex of borane and tetrahydrofuran, or borane and dimethyl sulfide.

22. The preparation method according to claim 16, wherein the temperature for mixing is 25° C. to 35° C.

* * * * *